US010376535B2

(12) United States Patent
Moore et al.

(10) Patent No.: US 10,376,535 B2
(45) Date of Patent: Aug. 13, 2019

(54) THERAPY FOR MALIGNANT DISEASE

(71) Applicant: UNIVERSITY OF ROCHESTER, Rochester, NY (US)

(72) Inventors: Richard G. Moore, Victor, NY (US); Rakesh K. Singh, Barrington, RI (US); Naohiro Yano, Lincoln, RI (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 15/561,466

(22) PCT Filed: Mar. 28, 2016

(86) PCT No.: PCT/US2016/024566
§ 371 (c)(1),
(2) Date: Sep. 25, 2017

(87) PCT Pub. No.: WO2016/154629
PCT Pub. Date: Sep. 29, 2016

(65) Prior Publication Data
US 2018/0117075 A1 May 3, 2018

Related U.S. Application Data

(60) Provisional application No. 62/138,836, filed on Mar. 26, 2015.

(51) Int. Cl.
| | |
|---|---|
| *A61K 48/00* | (2006.01) |
| *C07H 21/02* | (2006.01) |
| *A61K 31/7105* | (2006.01) |
| *A61K 45/06* | (2006.01) |
| *A61K 31/5025* | (2006.01) |
| *A61K 31/58* | (2006.01) |
| *A61K 31/713* | (2006.01) |
| *A61P 35/00* | (2006.01) |
| *A61K 33/24* | (2019.01) |
| *A61K 45/00* | (2006.01) |
| *G01N 33/574* | (2006.01) |

(52) U.S. Cl.
CPC ...... *A61K 31/7105* (2013.01); *A61K 31/5025* (2013.01); *A61K 31/58* (2013.01); *A61K 31/713* (2013.01); *A61K 33/24* (2013.01); *A61K 45/05* (2013.01); *A61K 45/06* (2013.01); *A61K 48/0016* (2013.01); *A61K 48/0066* (2013.01); *A61P 35/00* (2018.01); *G01N 33/57484* (2013.01); *A61K 2300/00* (2013.01); *C12N 2310/11* (2013.01); *C12N 2310/122* (2013.01)

(58) Field of Classification Search
CPC .......................... A61K 31/713; C12N 15/111
See application file for complete search history.

(56) References Cited

U.S. PATENT DOCUMENTS

| | | |
|---|---|---|
| 4,708,871 A | 11/1987 | Geysen |
| 4,833,092 A | 5/1989 | Geysen |
| 5,194,599 A | 3/1993 | Froehler et al. |
| 5,223,409 A | 6/1993 | Ladner et al. |
| 5,403,484 A | 4/1995 | Ladner et al. |
| 5,527,899 A | 6/1996 | Froehler |
| 5,541,306 A | 7/1996 | Agrawal et al. |
| 5,550,111 A | 8/1996 | Suhadolnik et al. |
| 5,556,762 A | 9/1996 | Pinilla et al. |
| 5,563,253 A | 10/1996 | Agrawal et al. |
| 5,565,555 A | 10/1996 | Froehler et al. |
| 5,571,689 A | 11/1996 | Heuckeroth et al. |
| 5,571,799 A | 11/1996 | Tkachuk et al. |
| 5,587,361 A | 12/1996 | Cook et al. |
| 5,596,086 A | 1/1997 | Matteucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,646,269 A | 7/1997 | Matteucci et al. |
| 5,663,143 A | 9/1997 | Ley et al. |
| 5,663,312 A | 9/1997 | Chaturvedula |
| 5,672,697 A | 9/1997 | Buhr et al. |

(Continued)

FOREIGN PATENT DOCUMENTS

| | | |
|---|---|---|
| EP | 1212422 B1 | 2/2007 |
| WO | 84/03506 A1 | 9/1984 |

(Continued)

OTHER PUBLICATIONS

Drapkin et al. (Cancer Res, 2005, 65(6), pp. 2162-2169).*
Zhonghua Bing Li Xue Za Zhi, Effect of down-regulation of H E4 gene expression on biologic behavior of ovarian cancer cells, Oct. 2013, 42(10):687-90, abstract only (abstract is in office action).*
Bertrand et al. (Biochemical and Biophysical Research Communications, 296, 2002, 1000-1004).*
Brahmer et al. (N Engl J Med, 2012, 366(26), 2455-2465).*
Gatalica et al. (Cancer Epidemiol Biomarkers Prey, 23(12), 2014, pp. 2965-2970).*

(Continued)

*Primary Examiner* — Amy H Bowman
(74) *Attorney, Agent, or Firm* — Mintz Levin Cohn Ferris Glovsky and Popeo, P.C.; Ingrid A. Beattie

(57) ABSTRACT

Provided herein, inter alia, are methods and compositions directed to suppressing tumor cell growth in a subject as well as methods for sensitizing a proliferating cell for treatment with a cytotoxic agent via inhibiting expression of HE4 and one or more immune checkpoint inhibitors (ICIs). Also provided herein are methods for determining whether a subject who has been diagnosed with cancer would benefit from immunotherapy as well as methods for determining whether a subject with cancer is responding to immunotherapy via assessment of levels of HE4 gene and/or protein expression.

11 Claims, 12 Drawing Sheets

Specification includes a Sequence Listing.

(56) References Cited

U.S. PATENT DOCUMENTS

| | | |
|---|---|---|
| 5,677,437 A | 10/1997 | Teng et al. |
| 5,677,439 A | 10/1997 | Weis et al. |
| 5,721,218 A | 2/1998 | Froehler |
| 5,750,373 A | 5/1998 | Garrard et al. |
| 5,792,608 A | 8/1998 | Swaminathan et al. |
| 5,811,097 A | 9/1998 | Allison et al. |
| 5,855,887 A | 1/1999 | Allison et al. |
| 5,977,318 A | 11/1999 | Linsley et al. |
| 6,051,227 A | 4/2000 | Allison et al. |
| 6,207,156 B1 | 3/2001 | Kuchroo et al. |
| 6,682,736 B1 | 1/2004 | Hanson et al. |
| 6,984,720 B1 | 1/2006 | Korman et al. |
| 7,109,003 B2 | 9/2006 | Hanson et al. |
| 7,132,281 B2 | 11/2006 | Hanson et al. |
| 7,399,845 B2 | 7/2008 | Seth et al. |
| 2002/0039581 A1 | 4/2002 | Carreno et al. |
| 2002/0086014 A1 | 7/2002 | Korman et al. |
| 2005/0201994 A1 | 9/2005 | Korman et al. |
| 2007/0031844 A1 | 2/2007 | Khvorova et al. |
| 2014/0348854 A1 | 11/2014 | Moore et al. |

FOREIGN PATENT DOCUMENTS

| | | | |
|---|---|---|---|
| WO | 84/03564 A1 | 9/1984 | |
| WO | 98/42752 A1 | 10/1998 | |
| WO | 00/00823 A1 | 1/2000 | |
| WO | 00/37504 A2 | 6/2000 | |
| WO | 00/39585 A1 | 7/2000 | |
| WO | 01/14424 A2 | 3/2001 | |
| WO | 2004/035607 A2 | 4/2004 | |
| WO | 2007/081767 A2 | 7/2007 | |
| WO | 2007/081768 A2 | 7/2007 | |
| WO | 2007/146511 A2 | 12/2007 | |
| WO | WO 2008/095152 A2 * | 8/2008 | ........... C12N 15/111 |
| WO | 2012/170513 A2 | 12/2012 | |
| WO | 2015/157262 A1 | 10/2015 | |
| WO | 2016/154629 A1 | 9/2016 | |

OTHER PUBLICATIONS

Hodi, et al.; "Biologic activity of Cytotoxic T Lymphocyte-Associated Antigen 4 Antibody Blockade in previously Vaccinated Metastatic Melanoma and Ovarian Carcinoma Patients", Proc. Natl. Acad. Sci. USA; 100(8): 4712-4717, 2003.

International Search Report and the Written Opinion of the International Searching Authority, dated Aug. 8, 2016 for PCT/US2016/024566.

Camacho, et al., "Phase 1 Clinical Trial of Anti-CTLA4 Human Monoclonal Antibody CP-675,206 in Patients (Pts) with Advanced Solid Malignancies", Journal of Clinical Oncology, vol. 22, Supplement 14, Abstract No. 2505, 1 page.

Charbonneau, et al., "The Immune System in the Pathogenesis of Ovarian Cancer", Critical Reviews in Immunology, vol. 33, Issue 2, 2013, pp. 137-164.

Clackson, et al., "Making Antibody Fragments Using Phage Display Libraries", Nature, vol. 352, Issue 6336, Aug. 15, 1991, pp. 624-628.

Clarke, et al., "Intraepithelial T Cells and Prognosis in Ovarian Carcinoma: Novel Associations With Stage, Tumor Type, and BRCA1 Loss", Modern Pathology, vol. 22, 2009, pp. 393-402.

Clauss, et al., "A Locus on Human Chromosome 20 Contains Several Genes Expressing Protease Inhibitor Domains with Homology to Whey Acidic Protein", Biochemical Journal, vol. 368, Issue 1, Nov. 15, 2002, pp. 233-242.

Clemente, et al., "Prognostic Value of Tumor Infiltrating Lymphocytes in the Vertical Growth Phase of Primary Cutaneous Melanoma", Cancer, vol. 77, Issue 7, 1996, pp. 1303-1310.

Cwirla, et al., "Peptides on Phage: A Vast Library of Peptides for Identifying Ligands", Proceedings of the National Academy of Sciences, vol. 87, No. 16, Aug. 1990, pp. 6378-6382.

Database Genbank (Jul. 29, 2018) "Programmed Cell Death 1 Ligand 1 Isoform B Precursor [Homo sapiens]", GenBank, Reference Sequence: NP_001254635.1, 3 pages.

Database Genbank (Aug. 5, 2018) "Programmed Cell Death Protein 1 Precursor [Homo sapiens]", GenBank Reference Sequence: NP_005009.2, 3 pages.

Gilks, et al., "Distinction Between Serous Tumors of Low Malignant Potential and Serous Carcinomas Based on Global mRNA Expression Profiling", Gynecologic Oncology, vol. 96, Issue 3, Mar. 2005, pp. 684-694.

Hamanishi, "Programmed Cell Death 1 Ligand 1 and Tumor-infiltrating CD8+ T Lymphocytes are Prognostic Factors of Human Ovarian Cancer", PNAS, vol. 109, Issue 9, Feb. 27, 2007, pp. 3360-3365.

Hough, "Large-Scale Serial Analysis of Gene Expression Reveals Genes Differentially Expressed in Ovarian Cancer", Cancer Research, vol. 60, Issue 22, Nov. 15, 2000, pp. 6281-6287.

Hurwitz, et al., "CTLA-4 Blockade Synergizes With Tumor-Derived Granulocyte—Macrophage Colony-Stimulating Factor for Treatment of an Experimental Mammary Carcinoma", PNAS, vol. 95, Issue 17, 1998, pp. 10067-10071.

Hwang, et al., "Prognostic Significance of Tumor-Infiltrating T Cells in Ovarian Cancer: A Meta-Analysis", Gynecologic Oncology, vol. 124, Issue 2, Feb. 2012, pp. 192-198.

Kang, et al., "Linkage of Recognition and Replication Functions by Assembling Combinatorial Antibody Fab Libraries Along Phage Surfaces", PNAS, vol. 88, May 1991, pp. 4363-4366.

Kirchhoff, et al., "A Major Human Epididymis-Specific cDNA Encodes a Protein with Sequence Homology to Extracellular Proteinase Inhibitors", Biology of Reproduction, vol. 45, Issue 2, Aug. 1, 1991, pp. 350-357.

Kohler, et al., "Continuous Cultures of Fused Cells Secreting Antibody of Predefined Specificity", Nature, vol. 256, No. 5517, 1975, pp. 495-497.

Koshkin, et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, vol. 54, Issue 14, Apr. 2, 1998, pp. 3607-3630.

Lowman, et al., "Selecting High-Affinity Binding Proteins by Monovalent Phage Display", Biochemistry, vol. 30, Issue 45, Nov. 12, 1991, pp. 10832-10838.

Marks, et al., "By-Passing Immunization: Human Antibodies from V-Gene Libraries Displayed on Phage", Journal of Molecular Biology, vol. 222, Issue 3, Dec. 5, 1991, pp. 581-597.

Mokyr, et al., "Realization of the Therapeutic Potential of CTLA-4 Blockade in Low-Dose Chemotherapy-treated Tumor-bearing Mice", Cancer Research, vol. 58, Issue 23, 1998, pp. 5301-5304.

Moore, et al., "A Novel Multiple Marker Bioassay Utilizing HE4 and CA125 for the Prediction of Ovarian Cancer in Patients with a Pelvic Mass", Gynecologic Oncology, vol. 112, Issue 1, Jan. 2009, pp. 40-46.

Moore, et al., "Utility of a Novel Serum Tumor Biomarker HE4 in Patients with Endometrioid Adenocarcinoma of the Uterus", Gynecologic Oncology, vol. 110, Issue 2, Aug. 2008, pp. 196-201.

Mullard, "New Checkpoint Inhibitors Ride the Immunotherapy Tsunami", Nature Reviews Drug Discovery, vol. 12, Issue 7, Jul. 2013, pp. 486-492.

Sato, et al., "Intraepithelial CD8+ Tumor-Infiltrating Lymphocytes and a High CD8+/ Regulatory T Cell Ratio are Associated with Favorable Prognosis in Ovarian Cancer", PNAS, vol. 102, Issue 51, Dec. 20, 2005, pp. 18538-18543.

Schumacher, et al., "Prognostic Significance of Activated CD8+ T Cell Infiltrations within Esophageal Carcinomas", Cancer Research, vol. 61, Issue 10, May 15, 2000, pp. 3932-3936.

Smith, "Surface Presentation of Protein Epitopes Using Bacteriophage Expression Systems", Current Opinion in Biotechnology, vol. 2, Issue 5, Oct. 1991, pp. 668-673.

Wands, et al., "High Affinity Monoclonal Antibodies to Hepatitis B Surface Antigen (HB,Ag) Produced by Somatic Cell Hybrids", Gastroenterology, vol. 80, Issue 2, Feb. 1981, pp. 225-232.

(56) References Cited

OTHER PUBLICATIONS

Wang, et al., "Monitoring Gene Expression Profile Changes in Ovarian Carcinomas Using cDNA Microarray", Gene, vol. 229, Issue 1-2, Apr. 1999, pp. 101-108.
Wang, et al., "Checkpoint 1-6,8-16 inhibitors in immunotherapy of ovarian cancer", Tumor Biology, vol. 36, Issue 1, Nov. 20, 2014, pp. 33-39.
Zhang, et al., "Intratumoral T Cells, Recurrence, and Survival in Epithelial Ovarian Cancer", The New England Journal of Medicine, vol. 348, Issue 3, Jan. 16, 2003, pp. 203-213.
Supplementary European Search Report corresponding to European Patent Application No. 16769841, dated Oct. 2018, 6 pages.

* cited by examiner

THERAPY FOR MALIGNANT DISEASE

CROSS-REFERENCE TO RELATED APPLICATIONS

This application is the U.S. national phase, pursuant to 35 U.S.C. § 371, of PCT international application Ser. No. PCT/US2016/024566, filed Mar. 28, 2016, designating the United States and published on Sep. 29, 2016 as publication WO 2016/154629 A1, which claims priority to U.S. Provisional Application Ser. No. 62/138,836, filed Mar. 26, 2015. The entire contents of the aforementioned patent applications are incorporated herein by this reference.

FIELD OF INVENTION

The invention relates generally to the field of cancer therapeutic strategies.

BACKGROUND

Cancer is the leading cause of death in the United States for individuals in between the ages of forty and seventy-nine. In the United States alone, approximately 1,500 people die each day as a result of cancer. As such, there is a compelling need to develop new therapeutic strategies and methods for early detection and prognosis to improve treatment outcomes and overall patient survival.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY

The invention provided herein discloses, inter alia, methods for treating and diagnosing cancer (such as, ovarian cancer) via inhibiting and monitoring the levels of human epididymis protein 4 (HE4) and one or more immune checkpoint inhibitors (ICIs) in subjects diagnosed with or suspected of having cancer.

Accordingly, in some aspects, provided herein are methods for suppressing tumor cell growth in a subject comprising: concurrently or sequentially inhibiting (a) the activity or level of human epididymal secretory protein E4 (HE4) in the tumor cell; and (b) the activity or level of one or more immune checkpoint inhibitors (ICIs) in the cell, thereby suppressing tumor cell growth in the subject. In one embodiment, the activity or level of HE4 is inhibited, e.g., an HE4 inhibitor is administered, prior to inhibition of the activity or level of one or more ICIs, e.g., administration of an ICI. In other embodiments, the activity or level of HE4 is inhibited subsequent to inhibition of the activity or level of one or more ICIs, e.g., by administration of an ICI prior to administration of an HE4 inhibitor. In some embodiments, the activity or level of the ICI is inhibited by

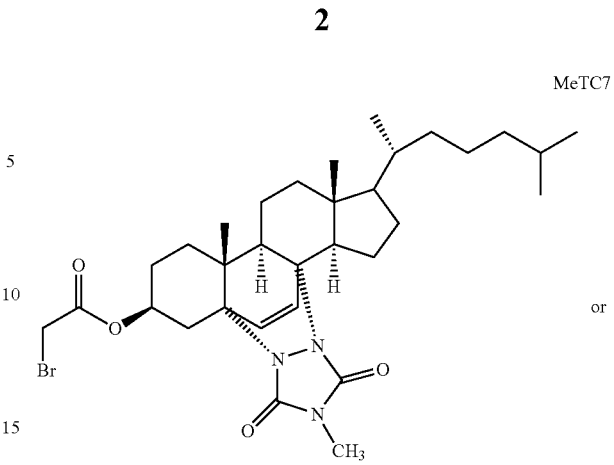
MeTC7

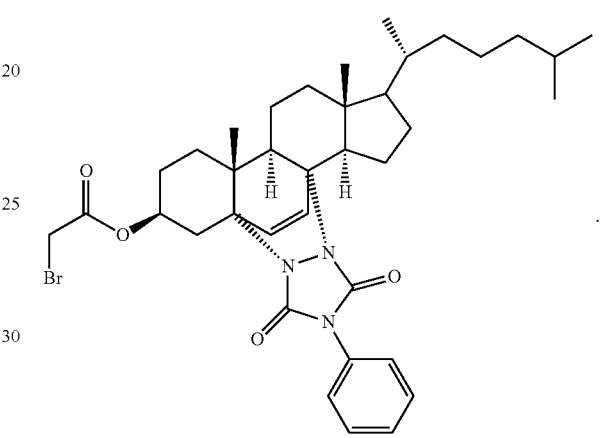
PTC7

In some embodiments, the tumor cell is a malignant tumor cell. In some embodiments, the tumor cell is a cancer progenitor cell or a cancer stem cell. For example, the methods are useful for treating "Müllerian cancers." In some embodiments, the malignant tumor cell an ovarian cancer cell, an endometrial cancer cell, or a breast cancer cell. In some embodiments of any of the embodiments disclosed herein, the level of HE4 in the tumor cell is inhibited by administering an effective amount of an HE4 inhibitor to the tumor cell. In some embodiments, the HE4 inhibitor is a neutralizing anti-HE4 antibody, an antisense oligonucleotide, a small interfering ribonucleic acid (siRNA), a small hairpin RNA (shRNA), a non-antibody binding polypeptide, or a small molecule chemical compound. In one embodiment, the HE4 inhibitor includes MT19c or PT19c:

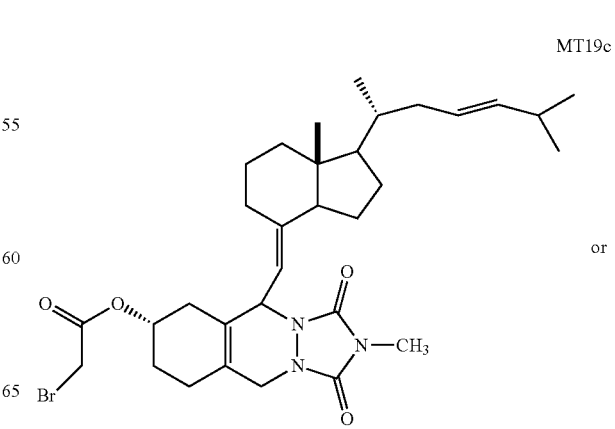
MT19c

-continued

PT19c

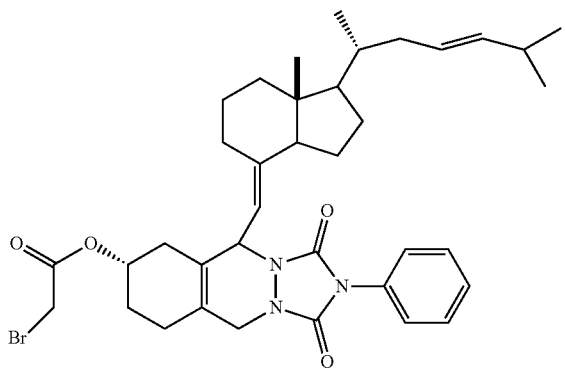

MeTC7

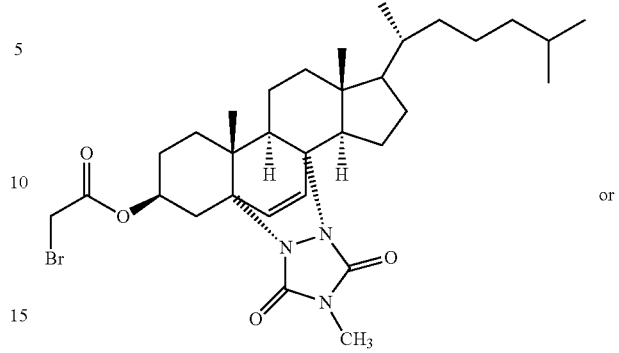

or

PTC7

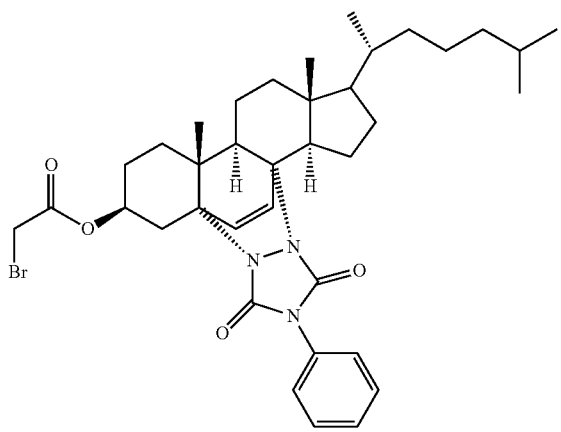

In some embodiments of any of the embodiments disclosed herein, the one or more ICIs are selected from the group consisting of CD80, CD28, CD86, cytotoxic T-lymphocyte-associated protein 4 (CTLA-4), Programmed death-ligand 1 (PD-L1), Programmed death-ligand 2 (PD-L2), Programmed cell death protein 1 (PD-1), Ligand of Inducible T-cell costimulator (L-ICOS), Inducible T-cell costimulator (ICOS), CD276, and V-set domain containing T cell activation inhibitor 1 (VTCN1). In some embodiments of any of the embodiments disclosed herein, the level of the one or more ICIs in the tumor cell is inhibited by administering an effective amount of an ICI inhibitor to the tumor cell. In some embodiments, the ICI inhibitor is selected from the group consisting of a neutralizing anti-ICI antibody, an antisense oligonucleotide, a small interfering ribonucleic acid (siRNA), a small hairpin RNA (shRNA), a non-antibody binding polypeptide, or a small molecule chemical compound. In some embodiments of any of the embodiments disclosed herein, the method further comprises administering a chemotherapeutic agent selected from the group consisting of an alkylating agent, an antimetabolite, an anthracycline, an antitumor antibiotic, a monoclonal antibody, a platinum agent, a plant alkaloid, a topoisomerase inhibitor, a vinca alkaloid, a taxane, and an epipodophyllotoxin. In some embodiments of any of the embodiments disclosed herein, the method further comprises administering a chemotherapeutic agent selected from the group consisting of cisplatin, carboplatin, paclitaxel, docetaxel, doxorubicin, camptothecin, and etoposide. In some embodiments of any of the embodiments disclosed herein, inhibition of the level if HE4 and inhibition of the level of one or more ICIs leads to a synergistic cytotoxic effect for suppressing tumor cell growth in the subject.

In other aspects, provided herein are methods for sensitizing a proliferating cell for treatment with a cytotoxic agent, the method comprising: concurrently or sequentially inhibiting (a) the activity or level of human epididymal secretory protein E4 (HE4) in the cell; and (b) the activity or level of one or more immune checkpoint inhibitors (ICIs) in the cell, wherein inhibiting the activity or levels of HE4 and the one or more immune checkpoint inhibitors sensitizes the cell for treatment with a cytotoxic agent. In some embodiments, the activity or level of the ICI is inhibited by In some embodiments, the proliferating cell is a tumor cell. In some embodiments, the tumor cell is a malignant tumor cell, such as all of a primer tumor or a metastatic tumor cell. In some embodiments, the tumor cell is a cancer progenitor cell or a cancer stem cell. In some embodiments, the malignant tumor cell an ovarian cancer cell, an endometrial cancer cell, or a breast cancer cell. In some embodiments of any of the embodiments disclosed herein, the level of HE4 in the cell is inhibited by administering an HE4 inhibitor to the tumor cell. In some embodiments, the HE4 inhibitor is a neutralizing anti-HE4 antibody, an antisense oligonucleotide, a small interfering ribonucleic acid (siRNA), a small hairpin RNA (shRNA), a non-antibody binding polypeptide, or a small molecule chemical compound. In one embodiment, the HE4 inhibitor comprises MT19c or PT19c.

In some embodiments of any of the embodiments disclosed herein, the one or more immune checkpoint inhibitors are selected from the group consisting of CD80, CD28, CD86, cytotoxic T-lymphocyte-associated protein 4 (CTLA-4), PD-L1, PD-L2, PD-1, Ligand or of Inducible T-cell costimulator (L-ICOS), Inducible T-cell costimulator (ICOS), CD276, and V-set domain containing T cell activation inhibitor 1 (VTCN1). In some embodiments of any of the embodiments disclosed herein, the level of the one or more ICIs in the tumor cell is inhibited by administering an effective amount of an ICI inhibitor to the tumor cell. In some embodiments, the ICI inhibitor is selected from the group consisting of a neutralizing anti-ICI antibody, an antisense oligonucleotide, a small interfering ribonucleic acid (siRNA), a small hairpin RNA (shRNA), a non-antibody binding polypeptide, or a small molecule chemical compound. In some embodiments of any of the embodiments disclosed herein, the method further comprises (c) contacting the cell with an effective amount of a cytotoxic agent. In some embodiments of any of the embodiments disclosed herein, wherein the cytotoxic agent is a chemotherapeutic agent. In some embodiments, the chemotherapeutic agent is selected from the group consisting of an alkylating agent, an antimetabolite, an anthracycline, an antitumor antibiotic, a monoclonal antibody, a platinum agent, a plant alkaloid, a topoisomerase inhibitor, a vinca alkaloid, a taxane, and an epipodophyllotoxin. In some embodiments, the chemotherapeutic agent is selected from the group consisting of cisplatin, carboplatin, paclitaxel, docetaxel, doxorubicin, camptothecin, and etoposide. In some embodiments of any of the embodiments disclosed herein, wherein inhibition of the level of HE4 and inhibition of the level of one or more ICIs leads to a synergistic sensitization effect in the cell for treatment with a cytotoxic agent.

In a further aspect, provided herein are kits comprising: (a) an HE4 inhibitor; and (b) one or more immune checkpoint inhibitor (ICI) inhibitors.

In still other aspects, provided herein are methods for determining whether a subject who has been diagnosed with cancer would benefit from immunotherapy, the method comprising: measuring the level of human epididymal secretory protein E4 (HE4) in a sample from the subject, wherein the subject will benefit from immunotherapy if the level of HE4 in the sample is higher than in one or more control samples acquired from one or more subjects without cancer, or a previously determined reference level obtained from a cohort of such subjects. In another aspect, provided herein are method s for determining whether a subject who has been diagnosed with cancer is responding to immunotherapy, the method comprising: measuring the level of human epididymal secretory protein E4 (HE4) in a sample from the subject, wherein the subject is determined to be responding to immunotherapy if the level of HE4 in the sample is less than the level of HE4 from one or more control samples acquired from one or more subjects who failed to respond to immunotherapy. In some embodiments, the subject would benefit from immunotherapy if the level of HE4 protein in the sample is >400 pM. In some embodiments, the subject is responding to immunotherapy if the level of HE4 protein in the sample is ≤400 pM. In some embodiments of any of the embodiments disclosed herein, the method is used to determine if the cancer has recurred or advanced. In some embodiments of any of the embodiments disclosed herein, the sample is a tissue sample, blood, serum, plasma, or urine. In some embodiments of any of the embodiments disclosed herein, the cancer is ovarian cancer or an ovarian tumor. In some embodiments, the ovarian cancer is ovarian cancer, fallopian tube cancer or primary peritoneal cancer. In some embodiments of any of the embodiments disclosed herein, the level of HE4 protein expression or a fragment thereof is measured. In some embodiments, the level of HE4 protein or a fragment thereof expression is measured by immunohistochemistry, enzyme-linked immunosorbant assay (ELISA), radioimmunoassay (RIA), Western or immunoblot, or another antibody-based method. In some embodiments, level of HE4 protein or a fragment thereof expression is measured by mass spectrometry or chromatography. In some embodiments of any of the embodiments disclosed herein, the level of HE4 gene expression is measured. In some embodiments, the level of HE4 gene expression is measured by qualitative reverse transcription polymerase chain reaction (qRT-PCR), RT-PCR or another PCR-based method, Northern Blot or serial analysis of gene expression (SAGE). In some embodiments of any of the embodiments disclosed herein, the immunotherapy comprises inhibiting (a) the activity or level of human epididymal secretory protein E4 (HE4) in the subject; and/or (b) the activity or level of one or more immune checkpoint inhibitors (ICIs) in the subject.

In another aspect, provided herein are methods for increasing the number of CD8+ T-cell lymphocytes or decreasing the activity or expression of PD-L1 in a subject in need thereof, the method comprising administering to the subject a therapeutically effective amount of at least one compound of formula (I) or a salt or solvate thereof:

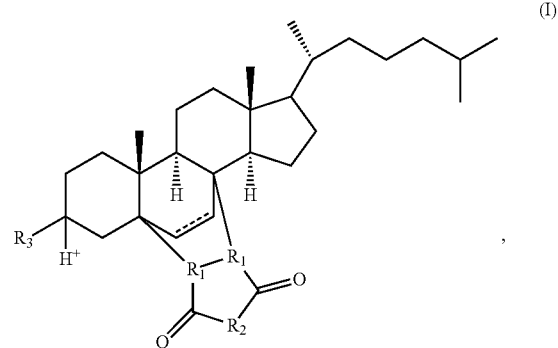

(I)

wherein in (I):

$R_1$ is $CR_5$ or N;

$R_3$ is selected from the group consisting of —N($R_5$)$_2$, —NO, —N($R_5$)N($R_5$)$_2$, $R_6$, —N($R_5$)—O$R_5$, —NH—C(=O)$R_5$, F, Cl, Br, I, hydroxy, alkoxy, mesyl, tosyl, —OSO$_3$H, —O(C$R_5$)n$R_6$, —O(C$R_5$)$_n$alkoxy, —(C$R_5$)$_{n+1}$OH, —OC(=O)(C$R_5$)$_n$R6, —OC(=O)(C$R_5$)$_n$O$R_5$, and —OC(=O)C($R_5$)=C($R_5$)$_2$;

or $R_3$ is selected from the group consisting of =O and =S, and H* is omitted;

$R_2$ is selected from the group consisting of O, S, C($R_4$)$_2$, and N($R_4$);

each occurrence of $R_4$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, OR5, and N($R_5$)$_2$;

each occurrence of $R_5$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, and substituted heteroarylalkyl;

$R_6$ is selected from the group consisting of F, Cl, Br, I, mesyl, tosyl, —OSi($R_5$)3, —C(=O)O$R_5$, and —C(=O)$R_5$;

the dotted line is a single or double bond; and, n is an integer ranging from 1 to 10, thereby increasing the number of CD8+ T-cell lymphocytes or decreasing the activity or expression of PD-L1. In some embodiments, the compound of formula (I) is In some embodiments, the activity or level of the ICI is inhibited by MeTC7

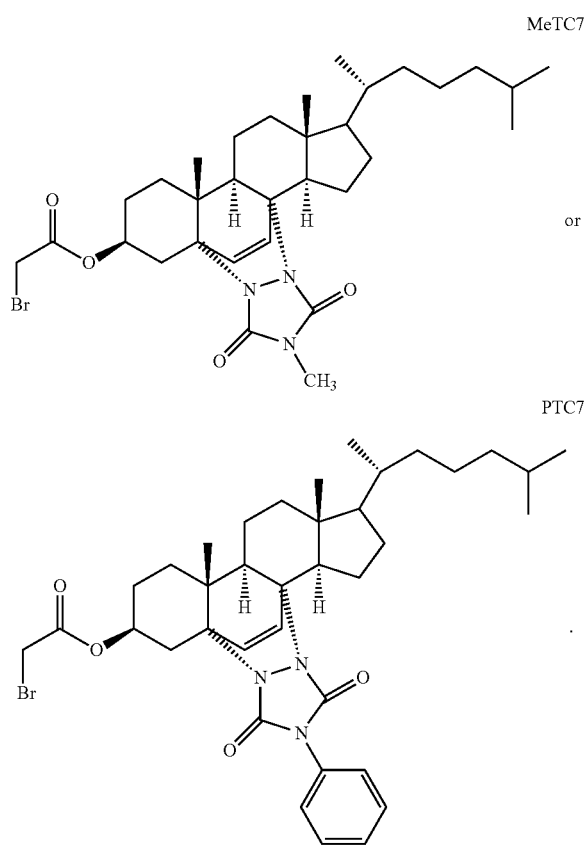

PTC7

In other aspects, provided herein is a use of a compound of formula (I) or a salt or solvate thereof:

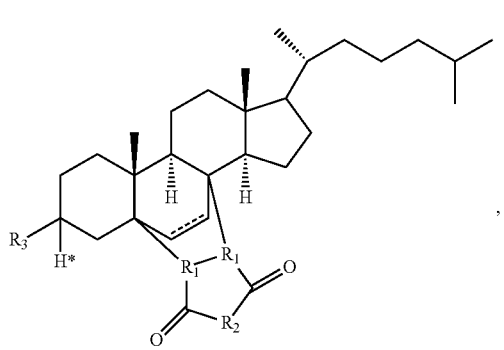

(I)

wherein in (I):
R$_1$ is CR$_5$ or N;
R$_3$ is selected from the group consisting of —N(R$_5$)$_2$, —NO, —N(R$_5$)N(R$_5$)$_2$, R$_6$, —N(R$_5$)—OR$_5$, —NH—C(=O)R$_5$, F, Cl, Br, I, hydroxy, alkoxy, mesyl, tosyl, —OSO$_3$H, —O(CR$_5$)nR$_6$, —O(CR$_5$)$_n$alkoxy, —(CR$_5$)$_{n+1}$OH, —OC(=O)(CR$_5$)$_n$—R6, —OC(=O)(CR$_5$)$_n$OR$_5$, and —OC(=O)C(R$_5$)=C(R$_5$)$_2$;
or R$_3$ is selected from the group consisting of =O and =S, and H* is omitted;
R$_2$ is selected from the group consisting of O, S, C(R$_4$)$_2$, and N(R$_4$);
each occurrence of R4 is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, OR5, and N(R$_5$)$_2$;
each occurrence of R5 is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, and substituted heteroarylalkyl;
R$_6$ is selected from the group consisting of F, Cl, Br, I, mesyl, tosyl, —OSi(R$_5$)3, —C(=O)OR$_5$, and —C(=O)R$_5$;
the dotted line is a single or double bond; and,
n is an integer ranging from 1 to 10,
for the manufacture of a medicament for use in inhibition of programmed death-ligand 1 (PD-L1) in cancer cells with our without an HE4 inhibitor. In some embodiments compound (I) is MeTC7

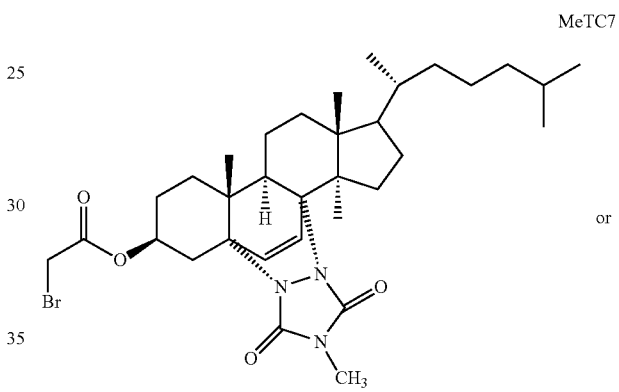

or

PTC7

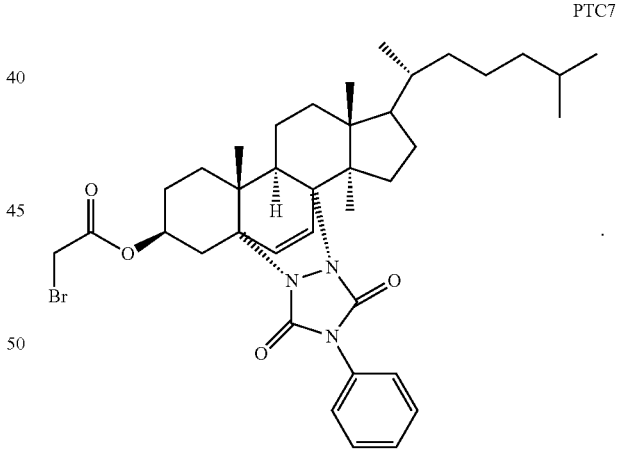

Each of the aspects and embodiments described herein are capable of being used together, unless excluded either explicitly or clearly from the context of the embodiment or aspect.

DETAILED DESCRIPTION

Figure 1:
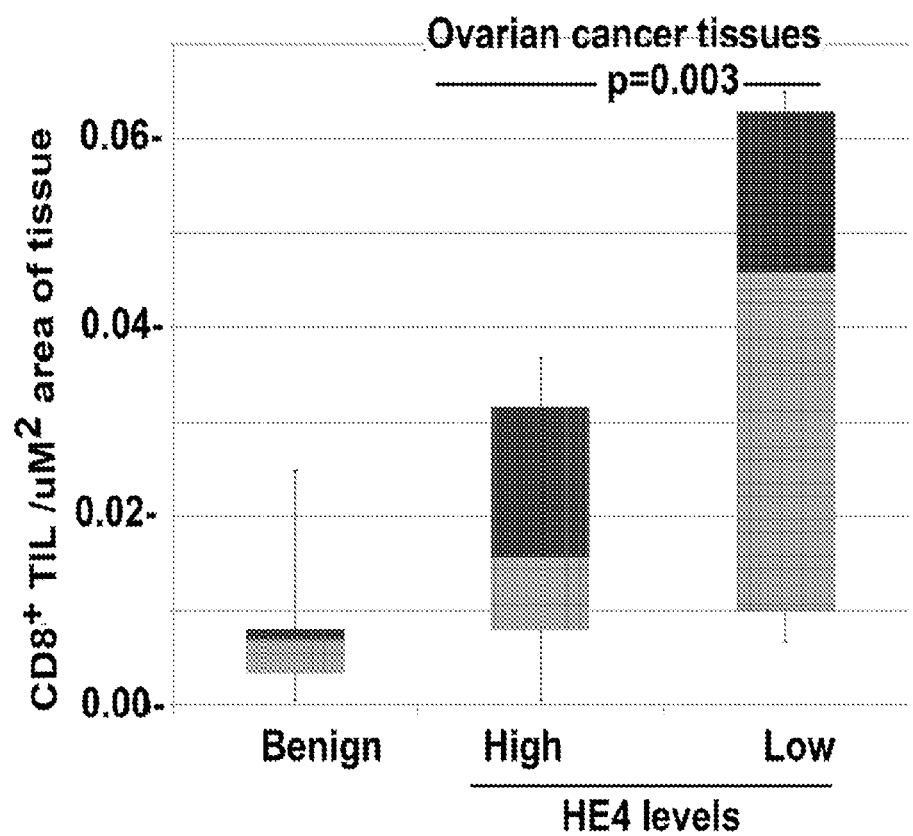
FIG. 1 depicts a bar graph showing HE4 levels correlate with reduced CD8+ T cell infiltration in ovarian tumors. Ovarian cancer tumors and benign tissues were stained for HE4 and CD8+ T cell-lymphocytes. HE4>400 pM Tumors were classified as high expressors and HE4<400 pM were classified as low expressors. CD8+ T cells were counted per μM² area in tumors of each group. The statistical correlation of intratumoral HE4 with number of CD8+ T-cell lymphocytes in the tumor specimen was analyzed. Serous carcinoma with high serum HE4 exhibit statistically lower number of CD8+ T-cell lymphocytes (p=0.003).

Approximately 1,500,000 new cancer cases were diagnosed in 2010, excluding the carcinoma in situ (noninvasive cancer), and basal and squamous cell skin cancer cases, which are not required to be reported to cancer registries. As such, there is a compelling need to develop new therapeutic strategies and methods for early detection and prognostication to improve treatment outcomes and overall patient survival Human epididymis protein 4 (HE4) was identified in the epithelium of the distal epididymis using Northern blot analysis and in situ transcript hybridization (Kirchhoff et al, 1991 Biol Reprod, 45:350-357). Subsequent studies using RNA dot blots, reverse transcription polymerase chain reaction (RT-PCR) and Northern blot analysis suggested that HE4 RNA expression is widespread (Clauss et al, 2002 Biochem J, 368:233-242). Previous studies using comparative genomic hybridization and in silico chromosomal clustering reported that human chromosome 20q12-13.2 is consistently amplified in ovarian carcinomas and harbors genes that may play causal roles in the pathogenesis of the disease. This region contains a cluster of 14 genes with homology to whey acidic protein (WAP). Among these genes is HE4 that is overexpressed in ovarian and endometrial cancers. The expression of HE4 protein is highly restricted in normal human tissues and is largely limited to the epithelium of the reproductive tracts and to the respiratory epithelium of the proximal airways. In malignant neoplasms, gene expression profiling has consistently identified up-regulation of HE4 in carcinoma of the ovary (Wang et al, 1999 Gene, 229: 101-108; Hough C D et al, 2000 Cancer Res, 60:6281-6287; Gilks C B et al, 2005 Gynecol Oncol, 96:684-694).

In malignant tumor tissues, HE4 is considered a biomarker for epithelial ovarian carcinoma (WO/2007/081768; WO/2007/081767; Moore R G et al, 2008 Gynecologic Oncology, 1 10: 196-201; Moore R G et al, 2009 Gynecologic Oncology, 1 12:40-46 and others). Similarly, malignancies of corpus uteri are also positive for HE4. (Drapkin R et al, 2005 Cancer Res, 65:2162-2169). HE4 is also a marker for other Müllerian-derived tumors. In cell line studies, secreted HE4 was also seen in cell lines that express endogenous HE4 RNA (e.g., CaOV-3 and OVCAR5). Intracellular immunofluorescence studies revealed that HE4 is distributed in a region of the cytoplasm, or endoplasmic reticulum and the Golgi apparatus organelles (Drapkin R et al, 2005 Cancer Res, 65:2162-2169).

T-cell lymphocyte infiltration has been shown to be indicative of a host immune response to the tumor and often correlated with favorable prognosis (Clemente et al., Cancer 1996; 77:1303-10; Schumacher et al., Cancer Res 2001; 61:3932-6). In ovarian cancer, Zhang et al. showed that infiltration of CD3+ T-lymphocytes correlates with increased progression-free and overall survival of patients (N Engl J Med 2003; 348:203-13). Further studies confirmed these findings and in particular CD8+ tumor infiltrating lymphocytes correlate with more favorable prognosis and increased survival (Sato et al., Proc Natl Acad Sci USA2005; 102:18538-43; Clarke et al., Mod Pathol 2009; 22:393-402; Hwang et al., Gynecol Oncol 2012; 124:192-8). The immune checkpoint inhibitor Programmed cell death 1 ligand 1 (PD-L1; GenBank: NP_001254635) was also noted to be prognostic in ovarian cancer (Hamanishi et al., Proc Natl Acad Sci USA2007; 104:3360-5). It is expressed on various adaptive immune effectors in the ovarian tumor microenvironment, including CD8 and CD4 cells, where it negatively regulates cell activation. Local immune suppression is mediated by myeloid-derived dendritic cells through PD-1/PD-L1 and by generating immune suppressive mediators such as arginase, indoleamine 2,3-dioxygenase, nitric oxide and reactive oxygen species (Charbonneau et al, Crit Rev Immunol. 2013; 33(2):137-164). In ovarian cancer, PD-1/PD-L1 is the dominant immune suppression mechanism by inhibiting anti-tumor activity of T cells. Blockade of PD-1, however, only results in partial anti-tumor effect due to release of immune regulatory cytokines, such as IL-10, IL-6, and G-CSF (Kirchhoff et al., Biol Reprod 1991, 45:350-357). The understanding of mechanisms of immune suppression is the key in being able to improve the treatment of ovarian cancer.

This invention provides, inter alia, methods for suppressing tumor cell growth in a subject as well as methods for sensitizing a proliferating cell for treatment with a cytotoxic agent. As disclosed herein, high expression levels of HE4 are inversely correlated with $CD8^+$ T cell infiltration in tumors. Carcinomas from subjects with high levels of serum HE4 exhibited statistically lower numbers of $CD8^+$ T cell lymphocytes compared to individuals with comparatively low serum levels of HE4. Also described herein are experiments demonstrating that HE4 and the immune checkpoint inhibitor (ICI) PD-L1 co-localize in the cells of normal, benign, and serous ovarian tumors. Further described herein are results showing that HE4 overexpression leads to significant overexpression of PD-L1 in cancer tissues and that inhibiting HE4 expression levels in cancerous tissues results in a contemporaneous decrease in the expression levels of PD-L1 in an in vivo cancer model. Additionally, shown herein are results demonstrating that exogenous recombinant HE4 activates the expression of PD-1 (GenBank: NP_005009) in donor peripheral blood mononuclear cells (PBMCs). Also shown herein are results showing that antisense knockdown of HE4 sensitizes a chemotherapy-resistant form of ovarian cancer to successful treatment with cisplatin. Based on the data described herein, it was determined that inhibition of levels of HE4 in combination with inhibition of one or more ICIs presents a novel approach to suppress tumor cell growth or to sensitize a proliferating cell for treatment with a cytotoxic agent. Prior to the invention described herein, the relationship between HE4 and ICI expression levels were unknown in the pathology of cancers (for example, ovarian cancers).

The present invention also provides methods for determining whether a subject who has been diagnosed with cancer would benefit from immunotherapy (directed to, for example, inhibition of expression levels of HE4 and one or more ICIs) as well as methods for determining whether a subject who has been diagnosed with cancer is responding to immunotherapy. As discussed above, high expression levels of HE4 and ICIs are associated with tumors having statistically lower levels of $CD8^+$ T cell lymphocyte infiltration. Accordingly, the methods provided herein represent a novel approach for determining both whether an individual would benefit from an immunotherapy as well as for monitoring the course of treatment in a subject undergoing such an immunotherapy, based on the assessment of expression levels of HE4 and ICIs.

The instant invention also provides methods for increasing the number of CD8+ T-cell lymphocytes in a tumor microenvironment or decreasing the expression or activity of the ICI PD-L1 in an individual who has been diagnosed with a proliferative disease (for example, cancer). As disclosed herein, administration of vitamin D receptor (VDR) antagonist 7-dehydrocholesterol derivatives reduced the expression of PD-L1 in multiple cancer cell lines. Significantly, this represents the first example of a small molecule chemical compound that is able to negatively regulate the expression or activity of PD-L1 in cancer cells.

I. Definitions

As used herein, the terms "immune checkpoint inhibitors" (ICIs), "checkpoint inhibitors," and the like refer to compounds that inhibit the activity of control mechanisms of the immune system. Immune system checkpoints, or immune checkpoints, are inhibitory pathways in the immune system that generally act to maintain self-tolerance or modulate the duration and amplitude of physiological immune responses to minimize collateral tissue damage. ICIs can inhibit an immune system checkpoint by inhibiting the activity of a protein in the pathway. ICI proteins include, but are not limited to, CD80, CD28, CD86, cytotoxic T-lymphocyte-associated protein 4 (CTLA-4), PD-L1, PD-L2, PD-1, Ligand of Inducible T-cell costimulator (L-ICOS), Inducible T-cell co-stimulator (ICOS), CD276, and V-set domain containing T cell activation inhibitor 1 (VTCN1). As such, ICI inhibitors include antagonists of, for example, ICIs such as CTLA4, PD1, or PD-L1. For example, antibodies that bind to CTLA4, PD-1, or PD-L1 and antagonize their function are ICI inhibitors. Moreover, any molecule (e.g., peptide, nucleic acid, small molecule, etc.) that inhibits the inhibitory function of an ICI is an ICI inhibitor.

As used herein, a "nucleic acid" or "oligonucleotide" refers to two or more deoxyribonucleotides and/or ribonucleotides covalently joined together in either single double-stranded form.

As used herein, an "isolated" or "purified" nucleic acid molecule, polynucleotide, polypeptide, protein or organic compound such as a small molecule (e.g., those described below), is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. For example, a purified DNA includes a cDNA. A purified or isolated polypeptide is free of the amino acids or sequences that flank it in its naturally-occurring state. Purified also defines a degree of sterility that is safe for administration to a human subject, e.g., lacking infectious or toxic agents.

"Small molecule compounds" refer to molecules less than 1000 daltons in molecular mass. Whether an organic compound or peptide, a small molecule compound is between 50-1000 daltons, e.g., less than 750 daltons, 500 daltons, 250 daltons or 100 daltons, in molecular mass. Small molecules include pharmaceutically active organic agents, biological agents, or peptides.

A "subject" can be a vertebrate, a mammal, or a human. Mammals include, but are not limited to, farm animals, sport animals, pets, primates, mice and rats. In one aspect, a subject is a human.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage.

As used herein, the phrase "ovarian cancer" can include ovarian cancer, fallopian tube cancer and primary peritoneal cancer as well as its various phenotypes.

By "ovarian tumor" it is meant any of epithelial carcinoma, sex cord carcinoma, germ cell carcinoma, metastatic carcinoma infiltrated in the pelvis or in the ovaries, cystadenoma, fibroma, thecoma, cystadenofibroma, mature teratoma, endometriosis, follicular cyst, abscess, struma ovarii, Leydig cell tumor, parasalpingeal cyst, hydrosalpinx, corpus luteum cyst, hemorrhagic cyst, tissue with calcifications NOS, necrotic tumor NOS or combinations thereof.

By the terms "effective amount" and "therapeutically effective amount" of a formulation or formulation component is meant a sufficient amount of the formulation or component to provide the desired effect. For example, by "an effective amount" is meant an amount of an HE4 and/or ICI inhibitor to treat cancer. Ultimately, the attending physician or veterinarian decides the appropriate amount and dosage regimen.

The phrase "inhibiting the activity of HE4 and/or one or more ICI inhibitors," as used herein, means inhibiting one or more or all of the biological and/or biochemical functions of HE4 and/or one or more ICI inhibitors without necessarily affecting (1) expression of the genes encoding HE4 and/or one or more ICI inhibitors and/or (2) expression of HE4 and/or one or more ICI inhibitor proteins or fragments thereof.

The phrase "inhibiting the level of HE4 and/or one or more ICI inhibitors," as used herein, means inhibiting the expression of HE4 and/or one or more ICI inhibitors at the level of DNA transcription into RNA or RNA translation into protein, thereby resulting in decreased or no HE4 and/or ICI RNA and/or protein in a cell. In some embodiments, inhibiting the level of HE4 and/or one or more ICI inhibitors encompasses manipulating a cell to cause proteolytic degradation of an HE4 and/or one or more ICI inhibitor protein. In some embodiments, inhibiting the level of HE4 and/or one or more ICI inhibitors encompasses manipulating a cell to cause degradation of an HE4 and/or one or more ICI inhibitor RNA.

"Synergism" or "synergistic," as used herein refers to the coordinated action of two or more agents (such as an HE4 inhibitor and one or more ICI inhibitor(s)) on the growth of a proliferating cell (such as a tumor cell) or the sensitivity of a proliferating cell to a cytotoxic agent whose effect is greater than additive.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl.

Certain specific examples include ($C_1$-$C_6$)alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Certain specific examples include ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl) crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—CCH. The term "homopropargylic" refers to a group exemplified by —$CH_2CH_2$—CCH. The term "substituted propargylic" refers to a group exemplified by —$CR_2$—CCR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—CCR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O) OH, trifluoromethyl, —C N, —C(=O)O($C_1$-$C_4$)alkyl, —C(=O)$NH_2$, —C(=O)NH($C_1$-$C_4$)alkyl, —C(=O)N (($C_1$-$C_4$)alkyl)$_2$, —$SO_2NH_2$, —C(=NH)$NH_2$, and —$NO_2$, advantageously containing one or two substituents selected from halogen, —OH, alkoxy, —$NH_2$, trifluoromethyl, —$N(CH_3)_2$, and —C(=O)OH, more advantageously selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. In certain embodiments, alkoxy includes ($C_1$-$C_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom, advantageously, fluorine, chlorine, or bromine, more advantageously, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$-0H, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of 0, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. In certain embodiments, aryl includes phenyl and naphthyl, in particular, phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Examples included aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Specific examples include substituted aryl($CH_2$)—. Similarly, the term "heteroaryl-($C_1$-$C_3$) alkyl" means a functional group wherein a one to three carbon alkylene chain is attached to a heteroaryl group, e.g., —$CH_2CH_2$-pyridyl. One embodiment is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Specific examples include substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzo thienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, in particular, straight.

The transitional term "comprising," which is synonymous with "including," "containing," or "characterized by," is inclusive or open-ended and does not exclude additional, unrecited elements or method steps. By contrast, the transitional phrase "consisting of excludes any element, step, or ingredient not specified in the claim. The transitional phrase "consisting essentially of limits the scope of a claim to the specified materials or steps "and those that do not materially affect the basic and novel characteristic(s)" of the claimed invention.

Unless defined otherwise herein, all technical and scientific terms used herein have the same meaning as commonly understood by one of ordinary skill in the an to which this invention pertains.

As used herein, the singular terms "a," "an," and "the" include the plural reference unless the context clearly indicates otherwise.

II. Methods of the Invention

A. Suppression of Proliferative Cell Growth and/or Tumor Cell Growth

The therapeutic methods disclosed herein are directed to concurrently or sequentially inhibiting the level of HE4 and one or more ICIs in a proliferative cell (such as a tumor cell) in order to suppress tumor cell growth in a subject or sensitize a proliferating cell for treatment with a cytotoxic agent.

The methods of the invention may be practiced in an adjuvant setting. "Adjuvant setting" refers to a clinical setting in which a subject has had a history of a proliferative disease, particularly cancer (such as ovarian cancer), and generally (but not necessarily) has been responsive to therapy, which includes, but is not limited to, surgery, radiotherapy, and chemotherapy. However, because of a history of the proliferative disease (such as a cancer, for example, ovarian cancer or a tumor), these subjects are considered at risk of developing that disease. Treatment or administration in the "adjuvant setting" refers to a subsequent mode of treatment. "Adjuvant therapy," as used herein refers to additional cancer treatment given after the primary treatment to lower the risk that the cancer will come back. Adjuvant therapy may include chemotherapy, radiation therapy, hormone therapy, targeted therapy, or biological therapy. Adjuvant therapy is often used after primary treatments, such as surgery or radiation. Adjuvant therapy given before the main treatment is called neoadjuvant therapy. This type of adjuvant therapy can also decrease the chance of the cancer coming back, and its often used to make the primary treatment, e.g., surgery or radiation treatment, more effective in reducing tumor burden.

The methods provided herein may also be practiced in a "neoadjuvant setting," that is, the method may be carried out before the primary/definitive therapy. In some aspects, the subject has previously been treated. In other aspects, the subject has not previously been treated. In some aspects, the treatment is a first line therapy. The subject may be a human or may be a non-human mammal.

The methods and compositions disclosed herein can be used to treat "Müllerian cancers." As used herein, the phrase "Müllerian cancer" or "Müllerian-derived tumors" indicates any cancer arising from any part of the female genital tract (such as, but not limited to, the uterus, fallopian tubes, ovaries and/or other female genital tract malignancies). In some embodiments, the term Müllerian cancer can refer to ovarian, fallopian tube, primary peritoneal, endometrial and uterine cancers, including all histologic sub types associated with the same, such as, but not limited to serous, endometrioid, clear cell, mucinous, undifferentiated, poorly differentiated, carcinosarcoma (MMMT), sarcoma germ cell tumors, and sex cord stromal tumors.

Carcinomas are cancers of epithelial origin. Carcinomas intended for treatment with the methods of this invention include, but are not limited to, acinar carcinoma, acinous carcinoma, alveolar adenocarcinoma, carcinoma adenomatosum, adenocarcinoma, carcinoma of adrenal cortex, alveolar carcinoma, alveolar cell carcinoma, basal cell carcinoma, carcinoma basocellular, basaloid carcinoma, basosquamous cell carcinoma, breast carcinoma, bronchioalveolar carcinoma, bronchiolar carcinoma, cerebriform carcinoma, cholangiocellular carcinoma, chorionic carcinoma, colloid carcinoma, comedocarcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliate adenoids, carcinoma exulcere, carcinoma fibrosum, gelatinform carcinoma, gelatinous carcinoma, giant cell carcinoma, gigantocellulare, glandular carcinoma, granulose cell carcinoma, hair matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lentivular carcinoma, carcinoma lenticulare, lipomatous carcinoma, lymphoepithelial carcinoma, carcinoma mastotoids, carcinoma medullare, medullary carcinoma, carcinoma melanodes, melanotonic carcinoma, mucinous carcinoma, carcinoma muciparum, carcinoma mucocullare, mucoepidermoid carcinoma, mucous carcinoma, carcinoma myxomatodes, masopharyngeal carcinoma, carcinoma nigrum, oat cell carcinoma, carcinoma ossificans, osteroid carcinoma, ovarian carcinoma, papillary carcinoma, periportal carcinoma, preinvasive carcinoma, prostate carcinoma, renal cell carcinoma of kidney, reserve cell carcinoma, carcinoma sarcomatodes, scheinderian carcinoma, scirrhous carcinoma, carcinoma scrota, signet-ring cell carcinoma, carcinoma simplex, small cell carcinoma, solandoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberrosum, tuberous carcinoma, verrucous carcinoma, carcinoma vilosum.

The invention also provides methods and agents to treat sarcomas. Sarcomas are mesenchymal neoplasms that arise in bone and soft tissues. Different types of sarcomas are recognized and these include: liposarcomas (including myxoid liposarcomas and pleomorphic liposarcomas), leiomyosarcomas, rhabdomyosarcomas, neurofibrosarcomas, malignant peripheral nerve sheath tumors, Ewing's tumors (including Ewing's sarcoma of bone, extraskeletal or nonbone) and primitive neuroectodermal tumors (PNET), synovial sarcoma, hemangioendothelioma, fibrosarcoma, desmoids tumors, dermatofibrosarcoma protuberance (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) and osteosarcoma (also known as osteogenic sarcoma-skeletal and extra-skeletal, and chondrosarcoma.

Optionally, the cancers to be treated are a refractory or a responding cancer. As used herein, a refractory cancer is a cancer that is resistant to the ordinary standards of care prescribed. These cancers, although initially responsive to treatment, recur and/or may be completely non responsive to the treatment. This invention can also be used to treat cancers that are immunogenic. Examples of immunogenic cancers include malignant melanoma and renal cell carcinoma, Mantel cell lymphoma, follicular lymphoma, diffuse large B-cell lymphoma, T-cell acute lymphoblastic leukemia, Burkitt Lymphoma, myeloma, immunocytoma, acute promyelocyte leukemia, chronic myeloid/acute lymphoblastic leukemia, acute leukemia, B-cell acute lymphoblastic leukemia, anaplastic large cell leukemia, myelodysplasia syndrome/acute myeloid leukemia, non-Hodgkin's lymphoma, chronic lymphocytic leukemia, acute myelogenous leukemia (AML), common (pre-B) acute lymphocytic leukemia, malignant melanoma, T-cell lymphoma, leukemia, B-cell lymphoma, epithelial malignancies, lymphoid malignancies, gynecologic carcinoma, biliary adenocarcinomas and ductal adenocarcinomas of the pancreas.

This invention also provides a method to inhibit angiogenesis in human subjects. Angiogenesis, the rapid proliferation of epithelial cells resulting in formation of new blood vessels, supports the progression and survival of tumors. As a secondary effect, angiogenesis may damage the various organs and tissues, eyes, skin, heart, blood vessels, lung, GI tract and genitourinary tract. Various methods or techniques available to assess angiogenesis, are not described herein may be used for the purpose of this invention. Methods and techniques to assess angiogenesis are known to those of ordinary skill in the art.

Further information related to HE4 and its role in cancer can be found in U.S. Patent Application Publication No. 20140348854, the disclosure of which is incorporated by reference herein.

B. Methods for Determining Whether a Subject would Benefit from Immunotherapy or is Responding to Immunotherapy Effective methods for determining whether a subject would benefit from immunotherapy or whether a subject with cancer is responding to immunotherapy are provided herein. These methods encompass detecting the expression level of an HE4 protein or fragment thereof or nucleic acid in a patient sample and comparing it relative to the level of HE4 from one or more control samples derived from subjects how have not been diagnosed with cancer or who have not responded to immunotherapy, respectively. High levels of HE4 compared to controls that have not been diagnosed with cancer suggest that the subject would benefit from immunotherapy. In contrast, low levels of HE4 compared to HE4 levels from controls who have not responded to immunotherapy suggests that the subject is benefiting from immunotherapy. In some embodiments, the immunotherapy encompasses inhibiting the expression of HE4 and/or one or more ICI, such as by any of the methods disclosed herein. In other embodiments, the subject would benefit from immunotherapy if the level of HE4 protein in the sample is greater than about 400 pM, such as greater than about 425 pM, 450 pM, 475 pM, 500 pM, 525 pM, 550 pM, 575 pM, 600 pM, 625 pM, 650 pM, 675 pM, 700 pM, 725 pM, 750 pM, 775 pM, 800 pM, 825 pM, 850 pM, 875 pM, 900 pM, 925 pM, 950 pM, 975 pM, or 1000 pM, or greater, inclusive of all values falling within this range. In other embodiments, the subject is responding to immunotherapy if the level of HE4 protein in the sample is less than or equal to about 400 pM, such as any of about 375 pM, 350 pM, 325 pM, 300 pM, 275 pM, 250 pM, 225 pM, 200 pM, 175 pM, 150 pM, 125 pM, 100 pM, 75 pM, 50 pM, 25 pM, or 0 pM, inclusive of all values falling within this range.

HE4 protein or nucleic acid expression levels can be used as a biomarker to determine whether a subject with cancer will respond to an immunotherapy or for determining whether a subject with cancer (such as, but not limited to, ovarian cancer, uterine cancer, or endometrial cancer) would benefit from immunotherapy by assessing the expression levels of an HE4 gene, protein or fragment thereof in a biological sample from a subject or subpopulation of subjects diagnosed with or suspected of having or developing cancer. As used herein, "HE4 gene or protein or fragment thereof expression level," or variants of the same, encompasses the existence of the full and intact HE4 DNA sequence (including, e.g., promoter elements, enhancer sequences, introns, and exons), the conversion of the HE4 DNA gene sequence into transcribed mRNA (including, e.g., the initial unspliced mRNA transcript or the mature processed mRNA), and/or the translated HE4 protein product (including, e.g. any posttranslational modifications such as, but not limited to, ubiquitination, sumoylation, acetylation, methylation, glycosylation, and/or hydroxylation).

Assessment of HE4 expression levels can be at the levels of protein, mRNA, or DNA. Assessment of mRNA expression levels of gene transcripts is routine and well known in the art. For example, one flexible and sensitive quantitative method for assessing mRNA expression levels in a biological sample is by quantitative RT-PCR (qRT-PCR) or by any other comparable quantitative PCR-based method. Additional methods for assessing HE4 mRNA expression include, but are not limited to, Northern blotting, microarrays, in situ hybridization, and serial analysis of gene expression (SAGE).

Similarly, assessments of HE4 protein (or a fragment thereof) expression levels are routine in the art. For example, one method of measuring protein levels is via. Western blotting or immunohistochemistry using commercially-available antibodies to HE4. However, without being bound to theory, there is a correlation between the expression level of HE4 and the likelihood that a subject with cancer (such as, but not limited to, ovarian cancer, endometrial cancer, or uterine cancer) would benefit from immunotherapy or whether a subject with cancer is responding to immunotherapy. Consequently, the sensitivity of the protein assay is particularly important. Therefore, RIA, ELISA, flow cytometry, or any other more sensitive quantitative method of measuring HE4 protein expression can be used instead of less quantitative methods.

C. Methods for Increasing the Number of CD8+ T Cell-Lymphocytes or Decreasing the Expression or Activity of PD-L1.

Also provided herein are methods for increasing the number of CD8+ T cell lymphocytes or decreasing the expression or activity of PD-L1 in a subject in need thereof by administration of a vitamin D receptor antagonist, such as any of the 7-dehydrocholesterol derivatives described herein (for example, MeTC7). As discussed in Example 8, treatment of ovarian and medulloblastoma cancer cell lines (but not melanoma) with MeTC7 downregulated the expression of PD-L1 in these cells.

PD-L1 is expressed on various adaptive immune effectors in the tumor microenvironment, including CD8 cells, where it negatively regulates T-cell activation. In ovarian cancer, PD-1/PD-L1 is the dominant immune suppression mechanism by inhibiting anti-tumor activity of T cells.

Accordingly, administration of an vitamin D receptor antagonist, such as any of the 7-dehydrocholesterol derivatives described herein (for example, MeTC7) to a subject in need thereof (for example, a subject diagnosed with cancer) increases the number of CD8+ T-cell lymphocyte in the subject (for example, in a tumor microenvironment) by any of about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% or more. Determination of increased CD8+ T-cell lymphocytes following treatment with a VDR antagonist can be determined using any available means known in the art (for example, immunocytochemistry, flow cytometry, etc.).

Similarly, administration of a vitamin D receptor antagonist, such as any of the 7-dehydrocholesterol derivatives described herein (for example, MeTC7) to a subject in need thereof (for example, a subject diagnosed with cancer) can decrease the expression or activity level of PD-L1. Defined herein, "decreasing the expression or activity level of PD-L1" refers to either decreasing the level of PD-L1 gene expression or PD-L1 protein concentration within a cell or preventing PD-L1 protein from functioning with respect to its ability to negatively regulate T-cell activation. Thus, the methods of the present invention encompass decreasing the expression or activity level of PD-L1 by any of about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% or more. Determination of the expression levels or activity of PD-L1 can be performed by any number of assays known in the art.

III. Compositions

A. Inhibition of HE4 and One or More ICI Expression Levels

The therapeutic methods disclosed herein encompass concurrently or sequentially inhibiting the level of HE4 and one or more ICIs in a proliferative cell (such as a tumor cell). In any of the methods disclosed herein, levels of HE4 and ICIs can be inhibited by any means, for example, by neutralizing antibodies, non-antibody binding polypeptides, small molecule chemical compounds, an inhibitory nucleic acid, or combinations thereof.

ICIs include any agent that blocks or inhibits in a statistically significant manner, the inhibitory pathways of the immune system. Illustrative ICIs that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+ (αβ) T cells), CD160 (also referred to as BY55), CGEN-15049, CHK 1 and CHK2 kinases, A2aR and various B-7 family ligands. B7 family ligands include, but are not limited to, B7-1, B7-2, B7-DC, B7-H1, B7-H2, B7-H3, B7-H4, B7-H5, B7-H6 and B7-H7. ICIs include antibodies, or antigen binding fragments thereof, other binding proteins, biologic therapeutics or small molecules, that bind to and block or inhibit the activity of one or more of CTLA-4, PDL1, PDL2, PD1, BTLA, HVEM, TIM3, GAL9, LAG3, VISTA, KIR, 2B4, CD160 and CGEN-15049. Illustrative ICIs include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Checkpoint protein ligands include, but are not limited to PD-L1, PD-L2, B7-H3, B7-H4, CD28, CD86 and TIM-3.

In one embodiment, the present invention covers the use of a specific class of ICIs are drugs that block the interaction between immune checkpoint receptor programmed cell death protein 1 (PD-1) and its ligand PD-L1. See A. Mullard, "New checkpoint inhibitors ride the immunotherapy tsunami," Nature Reviews: Drug Discovery (2013), 12:489-492. PD-1 is expressed on and regulates the activity of T-cells. Specifically, when PD-1 is unbound to PDL-1, the T-cells can engage and kill target cells. However, when PD-1 is bound to PDL-1 it causes the T-cells to cease engaging and killing target cells. Furthermore, unlike other checkpoints, PD-1 acts proximately such the PDLs are overexpressed directly on cancer cells which leads to increased binding to the PD-1 expressing T-cells.

One aspect of the present disclosure provides ICIs which are antibodies that can act as agonists of PD-1, thereby modulating immune responses regulated by PD-1. In one embodiment, the anti-PD-1 antibodies can be antigen-binding fragments. Anti-PD-1 antibodies disclosed herein are able to bind to human PD-1 and agonize the activity of PD-1, thereby inhibiting the function of immune cells expressing PD-1.

In one embodiment, the present invention covers the use of a specific class of ICIs are drugs that inhibit CTLA-4. Suitable anti-CTLA4 antagonist agents for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., Proc. Natl. Acad.

Sci. USA, 95(17):10067-10071 (1998); Camacho et al., J. Clin. Oncology, 22(145):Abstract No. 2505 (2004) (antibody CP-675206); Mokyr et al., Cancer Res., 58:5301-5304 (1998), and U.S. Pat. Nos. 5,977,318, 6,682,736, 7,109,003, and 7,132,281.

Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway, among other anti-CTLA4 antagonists.

In one embodiment, the present invention covers the use of a specific class of ICI are drugs that inhibit TIM-3. Blocking the activation of TIM-3 by a ligand, results in an increase in Th1 cell activation. Furthermore, TIM-3 has been identified as an important inhibitory receptor expressed by exhausted CD8+ T cells. TIM-3 has also been reported as a key regulator of nucleic acid mediated antitumor immunity. In one example, TIM-3 has been shown to be upregulated on tumor-associated dendritic cells (TADCs).

1. Antibodies

The methods disclosed herein encompass inhibiting the level of HE4 and one or more ICIs by administering one or more neutralizing antibodies directed to HE4 and one or more ICIs. "Antibody" as used herein is meant to include intact molecules as well as fragments which retain the ability to bind antigen (e.g., Fab and F(ab') fragments). These fragments are typically produced by proteolytically cleaving intact antibodies using enzymes such as a papain (to produce Fab fragments) or pepsin (to produce F(ab')$_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., Nature 256:495 (1975)). In general, this technology involves immunizing an animal, usually a mouse, with the CA125 peptide. The splenocytes of the immunized animals are extracted and fused with suitable myeloma cells, e.g., SP2O cells. After fusion, the resulting hybridoma cells are selectively maintained in a culture medium and then cloned by limiting dilution (Wands, et al., Gastroenterology 80:225-232 (1981)). The cells obtained through such selection are then assayed to identify clones which secrete antibodies capable of binding to HE4 and one or more ICI proteins or fragments thereof.

2. Non-Antibody Binding Polypeptides

The methods disclosed herein encompass inhibiting the level of HE4 and one or more ICIs by administering one or more non-antibody binding polypeptides directed to HE4 and/or one or more ICIs. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to HE4 and/or one or more ICIs. Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Cwirla, S. E. et al., (1990) Proc. Natl. Acad. Sci. USA, 87:6378; Lowman, H. B. et al., (1991) Biochemistry, 30:10832; Clackson, T. et al., (1991) Nature, 352: 624; Marks, J. D. et al., (1991), J. Mol. Biol., 222:581; Kang, A. S. et al., (1991) Proc. Natl. Acad. Sci. USA, 88:8363, and Smith, G. P. (1991) Current Opin. Biotechnol., 2:668).

3. Small Molecule Chemical Compounds

The methods disclosed herein encompass inhibiting the level of HE4 and one or more ICIs by administering one or more small molecule chemical compounds directed to directed to HE4 and/or one or more ICIs. The small molecule chemical compound may be a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule (such as HE4 and/or one or more ICIs) or mediating a biological activity of interest (such as, but not limited to, inhibition of cellular proliferation).

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library.

Small molecules may be identified and chemically synthesized using known methodology (see, e.g., International Patent Application Publication Nos. WO00/00823 and WO00/39585). Small molecules are usually less than about 2000 Daltons in size or alternatively less than about 1500, 750, 500, 250 or 200 Daltons in size, wherein such small molecules that are capable of binding, preferably specifically, to HE4 and/or one or more ICI gene, protein, or fragment thereof as described herein may be identified without undue experimentation using well known techniques. In this regard, it is noted that techniques for screening small molecule libraries for molecules that are capable of binding to a polypeptide target are well known in the art (see, e.g., PCT Publication Nos. WO00/00823 and WO00/39585). Small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

a. Small Molecule ICI Inhibitors

In one embodiment, the ICI inhibitor is a 7-dehydrocholesterol derivative. An example of a 7-dehydrocholesterol derivative suitable for use in the methods described herein include the compound of formula (I), or a salt or solvate thereof:

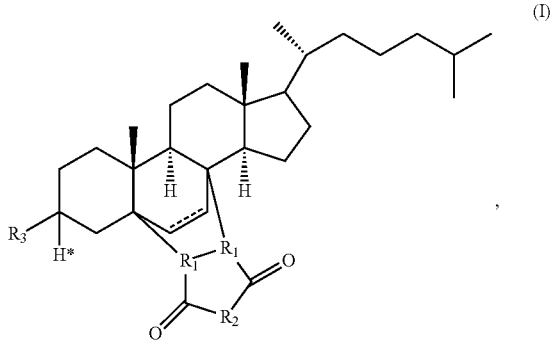

(I)

wherein in (I):

$R_1$ is $CR_5$ or N, wherein:

if $R_1$ is $CR_5$, then $R_3$ is selected from the group consisting of —$N(R_5)_2$, —NO, —$N(R_5)N(R_5)_2$, $R_6$, —$N(R_5)$—$OR_5$, —NH—C(=O)$R_5$, alkoxy, —$OSO_3H$, —O(CR_5)n$R_6$, —$O(CR_5)_n$ alkoxy, —$O(CR_5)_{n+1}OH$, —OC(=O)(CR_5)_nR_6$, —OC(=O)(CR_5)_nOR_5$, and —OC(=O)C(R_5)=C(R_5)_2$;

or $R_3$ is selected from the group consisting of =O and =S, and H* is omitted; and, if $R_1$ is N, then $R_3$ is selected from the group consisting of $N(R_5)_2$, —NO, —$N(R_5)N(R_5)_2$, $R_6$, —$N(R_5)$—$OR_5$, —NH—C(=O)$R_5$, Cl, Br, I, alkoxy, mesyl, tosyl, —$O(CR_5)nR_6$, —$O(CR_5)_{n+1}OR_5$, —OC(=O)(CR_5)_nR_6$, —OC(=O)(CR_5)_nOR_5$, and —OC(=O)C(R_5)=C(R_5)_2$;

$R_2$ is selected from the group consisting of O, S, $C(R_4)_2$, and $N(R_4)$;

each occurrence of $R_4$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, $OR_5$, and $N(R_5)_2$;

each occurrence of $R_5$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, and substituted heteroarylalkyl;

$R_6$ is selected from the group consisting of F, Cl, Br, I, mesyl, tosyl, —$OSi(R_5)3$, —C(=O)$OR_5$, and —C(=O)$R_5$;

the dotted line is a single or double bond; and, n is an integer ranging from 1 to 10.

In certain embodiments, the dotted line is a single bond. In other embodiments, the dotted line is a double bond.

In certain embodiments, the compound of formula (I) is the compound of formula (Ia), or a salt or solvate thereof:

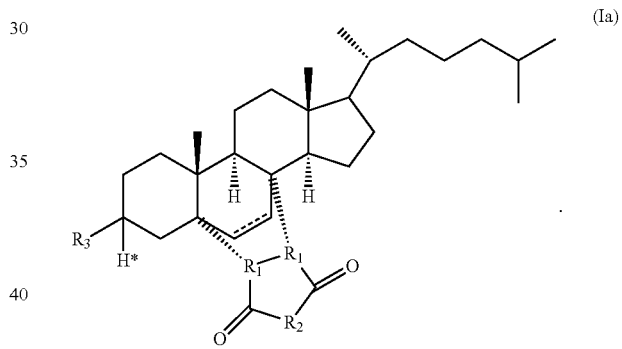

(Ia)

In certain embodiments, the compound of formula (I) is the compound of formula (Ib), or a salt or solvate thereof:

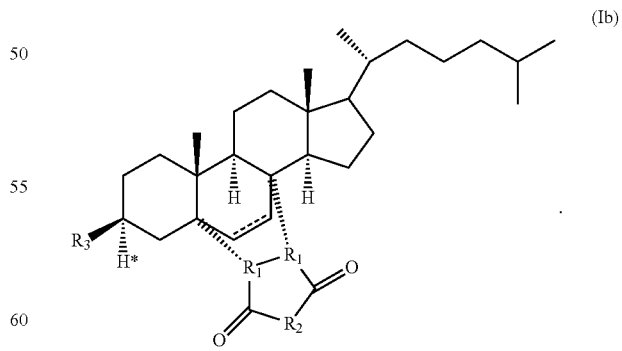

(Ib)

In certain embodiments, $R_1$ is N. In other embodiments, $R_2$ is $N(R_4)$.

In certain embodiments, the compound of formula (I) is the compound of formula (Ic), or a salt or solvate thereof:

In certain embodiments, the compound of formula (I) is the compound of formula (Ic), or a salt or solvate thereof:

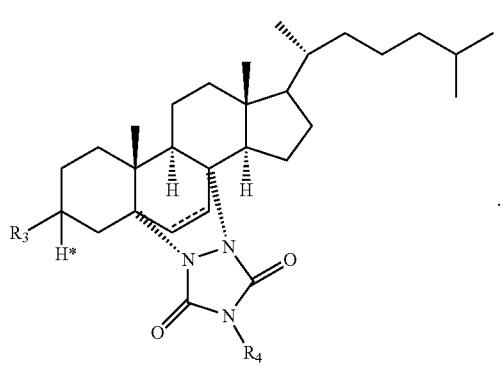
(Ic)

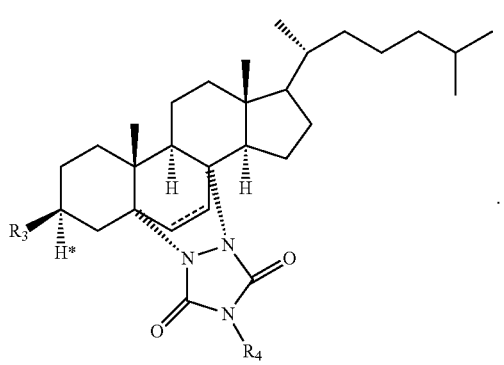
(Id)

In certain embodiments, $R_3$ is selected from the group consisting of —O(CR$_5$)$_2$. $R_6$, —OC(=O)(CR$_5$)$_n$—R6, —OC(=O)(CR$_5$)$_n$OR$_5$, and —OC(=O)C(R$_5$)=C(R$_5$)$_2$.

In certain embodiments, the compound of formula (I) is selected from the group consisting of:

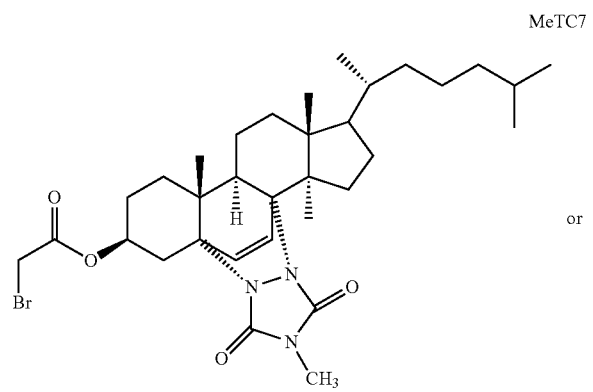
MeTC7 or

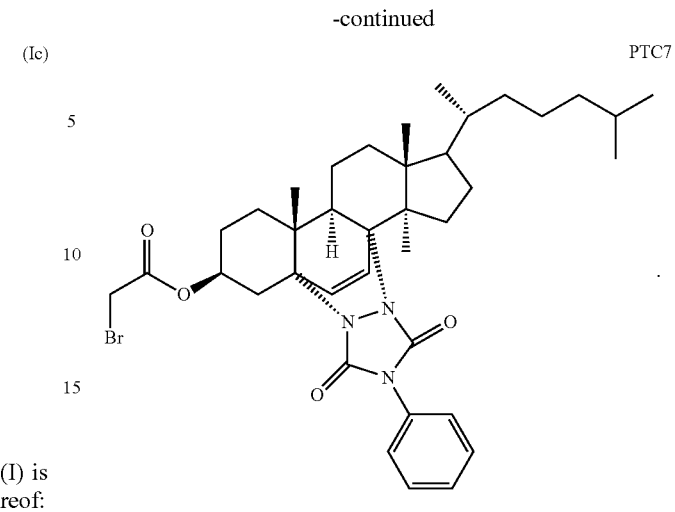
PTC7

In certain embodiments, $R_1$ is CR$_5$. In other embodiments, $R_5$ is selected from the group consisting of H, alkyl, substituted alkyl, cycloalkyl, substituted cycloalkyl, arylalkyl, substituted arylalkyl, heteroarylalkyl, and substituted heteroarylalkyl. In yet other embodiments, $R_3$ is selected from the group consisting of $R_6$, —O(CRs)$_n$R6, OC(=O)(CR$_5$)$_n$R$_7$, and OC(=O)C(R5)=C(R5)$_2$; or $R^3$ is selected from the group consisting of =O and =S, and H* is omitted.

In certain embodiments, n is 1, 2, 3, 4, or 5.

In certain embodiments, the small molecule chemical compound for use in any of the presently described methods is MeTC7.

MeTC7 and PTC7 were synthesized as shown below by addition of 1,2,4-triazolinedione (0.22 millimoles) to a solution of commercially available 7 dehydrocholesterol (7DHC) (0.2 millimoles in ethyl acetate) under nitrogen atmosphere, and the system was stirred under the dark at 0-4° C. for 3 hours. The pink color eventually disappeared. The solvent was removed under vacuum. The residue crude dry residue (0.07 millimoles) was added to a stirred suspension of bromoacetic acid and dicyclohexylcarbodiimide (DCC) in dichloromethane at 0-4° C. under a nitrogen gas atmosphere. The reaction mixture was stirred overnight, filtered to remove the resulting dicyclohexyl urea. The clear solution was evaporated and concentrated under reduced pressure to generate an oily residue, which was purified by preparative TLC. The well resolved band was extracted with 20% methanol in dichloromethane, and the compound was isolated by evaporating the solvent under the reduced pressure, to produce a white to pale yellow solid (yield: 35-75% depending on the batch).

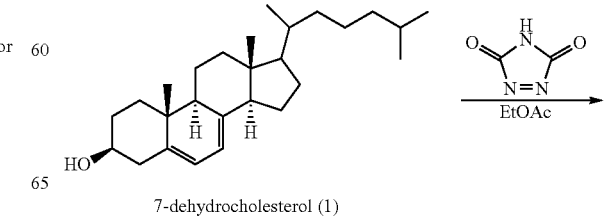

7-dehydrocholesterol (1)

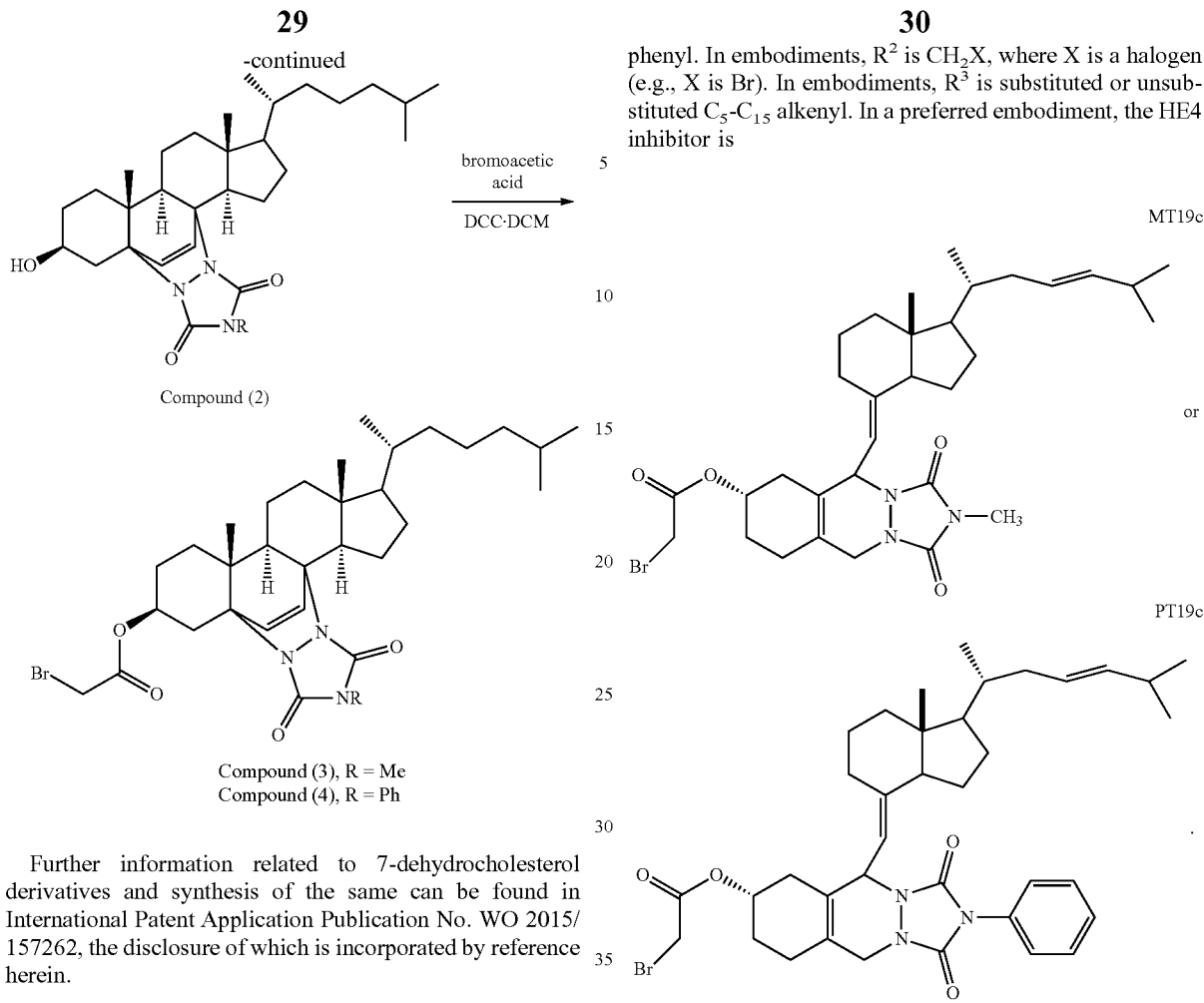

Compound (2)

Compound (3), R = Me
Compound (4), R = Ph

Further information related to 7-dehydrocholesterol derivatives and synthesis of the same can be found in International Patent Application Publication No. WO 2015/157262, the disclosure of which is incorporated by reference herein.

b. Small Molecule HE4 Inhibitors

The HE4 inhibitor can also be a small molecule chemical compound. In embodiments, an HE4 inhibitor has a structure according to the following formula,

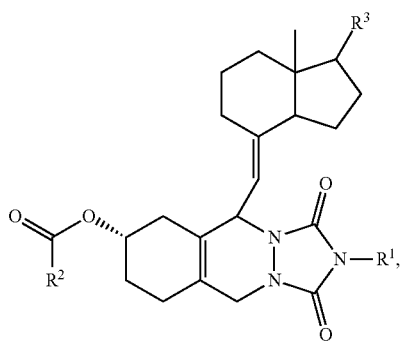

wherein
$R^1$ is substituted or unsubstituted $C_1$-$C_{12}$ alkyl, substituted or unsubstituted two- to twelve-membered heteroalkyl, substituted or unsubstituted $C_6$-$C_{10}$ aryl, or substituted or unsubstituted five- to ten-membered heteroaryl; $R^2$ is $C_1$-$C_{12}$ alkyl comprising a halogen (e.g., F, Cl, Br, or I) substituent; and $R^3$ is substituted or unsubstituted $C_1$-$C_{15}$ alkyl; substituted or unsubstituted $C_2$-$C_{15}$ alkenyl; or substituted or unsubstituted $C_2$-$C_{15}$ alkynyl. In embodiments, $R^1$ is methyl or phenyl. In embodiments, $R^2$ is $CH_2X$, where X is a halogen (e.g., X is Br). In embodiments, $R^3$ is substituted or unsubstituted $C_5$-$C_{15}$ alkenyl. In a preferred embodiment, the HE4 inhibitor is MT19c or PT19c 4. Inhibitory Nucleic Acids The methods disclosed herein encompass inhibiting the level of HE4 and one or more ICIs by administering one or more inhibitory nucleic acids directed to HE4 and/or one or more ICIs. Such nucleic acids can include, without limitations, antisense oligonucleotides, small inhibitory RNAs (siRNAs), triplex-forming oligonucleotides, ribozymes, antisense Locked Nucleic Acids (LNAs) or any other inhibitory oligonucleotide or nucleic acid. In addition, the nucleic acid-based therapeutics for use in the methods described herein can have one or more alterations to the oligonucleotide phosphate backbone, sugar moieties, and/or nucleobase (such as any of those described herein) that increase resistance to degradation, such as by nuclease cleavage. Nucleic acids complementary to HE4 and/or one or more ICI genes or RNAs are at least about 10 (such as any of about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotides in length. In another embodiment, the nucleic acids can be between about 10-15, 15-20, 20-25, 25-30, 30-35, 35-40, 40-45, or 45-50 oligonucleotides in length. In one embodiment, the inhibitory nucleic acid is a Locked Nucleic Acid (LNA) longRNA GAPmer targeting HE4 comprising a sequence of 5'-TTGCTGAAAGTGGTTA-3' (SEQ ID NO:1) or 5'-AGAGTCCCGAAAAAGG-3'(SEQ ID NO:2). As used herein, a "Locked Nucleic Acid" refers to an RNA nucleotide having a ribose moiety modified with an extra bridge connecting the 2' oxygen and 4' carbon. The bridge "locks" the ribose in the 3'-endo (North) conformation, which is often found in A-form duplexes. LNA nucleotides can be mixed with DNA or RNA residues in the oligonucleotide whenever desired and hybridize with DNA or RNA according to Watson-Crick base-pairing rules. Such oligomers are synthesized chemically by means known in the art and are commercially available. The locked ribose conformation enhances base stacking and backbone pre-organization which significantly increases hybridization properties as well as resistance to nucleases (see, e.g., Koshkin et al., 1998, Tetrahedron 54 (14): 3607-30).

The naturally occurring internucleoside linkage of RNA and DNA is a 3' to 5 phosphodiester linkage. The nucleic acids used according to any of the methods disclosed herein can have one or more modified, i.e. non-naturally occurring, internucleoside linkages. With respect to therapeutics, modified internucleoside linkages are often selected over oligonucleotides having naturally occurring internucleoside linkages because of desirable properties such as, for example, enhanced cellular uptake, enhanced affinity for target nucleic acids, and increased stability in the presence of nucleases.

Oligonucleotides (such as an antisense oligonucleotide) having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific though nonlimiting examples of nucleic acids (such as antisense oligonucleotides) useful in the methods of the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In some embodiments, modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphospho-triesters, selenophosphates and boranophosphates having normal 3 '-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof) can also be employed. Various salts, mixed salts and free acid forms are also included.

Oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and C component parts.

Representative United States patents that teach the preparation of the above phosphorus-containing and non-phosphorus-containing linkages include, but are not limited to, U.S. Pat. Nos. 5,541,306; 5,550,111; 5,563,253; 5,571,799; 5,587,361; 5,194,599; 5,565,555; 5,527,899; 5,721,218; 5,672,697 and 5,625,050, 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified nucleic acids (such as antisense oligonucleotides) complementary to HE4 and/or one or more ICI DNA or RNA sequences used as anticancer therapies in conjunction with any of the methods disclosed herein may also contain one or more substituted or modified sugar moieties. For example, the furanosyl sugar ring can be modified in a number of ways including substitution with a substituent group, bridging to form a bicyclic nucleic acid "BNA" and substitution of the 4'-0 with a heteroatom such as S or N(R) as described in U.S. Pat. No. 7,399,845, hereby incorporated by reference herein in its entirety. Other examples of BNAs are described in published International Patent Application No. WO 2007/146511, hereby incorporated by reference herein in its entirety.

Nucleic acids (such as antisense oligonucleotides) for use in any of the methods disclosed herein may also include nucleobase (often referred to in the art simply as "base") modifications or substitutions. Nucleobase modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to oligonucleotide compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an oligonucleotide compound (such as an antisense oligonucleotide compound) for a target nucleic acid (such as HE4 and/or one or more ICIs).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

As used herein, "unmodified" or "natural" nucleobases include the purine bases adenine (A) and guanine (G), and the pyrimidine bases thymine (T), cytosine (C) and uracil (U).

B. Pharmaceutical Compositions

Any of the anticancer, anti-tumor, or proliferating cell-sensitization therapies (such as oligonucleotide-based therapies or small molecule chemical compound-based therapies) encompassed by any of the methods disclosed herein can be administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. When employed as oral compositions, the oligonucleotides and another disclosed herein are protected from acid digestion in the stomach by a pharmaceutically acceptable protectant.

This invention also includes pharmaceutical compositions which contain, as the active ingredient, one or more of the anticancer therapies disclosed herein associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The anticancer therapies disclosed herein are effective over a wide dosage range and are generally administered in a therapeutically effective amount. It will be understood, however, that the amount of the anticancer therapies actually administered will be determined by a physician, in the light of the relevant circumstances, including the condition to be treated, the chosen route of administration, the actual compound administered, the age, weight, and response of the individual patient, the severity of the patient's symptoms, and the like.

The tablets or pills can be coated or otherwise compounded to provide a dosage form affording the advantage of prolonged action and to protect the anticancer therapies (such as an oligonucleotide) from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described herein. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

C. Other Chemotherapeutic/Cytotoxic Agents

The methods and agents derived from this invention may be administered in combination with other therapies such as, for example, radiation therapy, surgery, conventional chemotherapy or with a combination of one or more additional therapies. The methods and agents derived from this invention may be administered alone in a pharmaceutical composition or combined with therapeutically effective and physiologically acceptable amount of one or more other active ingredients or agents. Such other active ingredient includes, but is not limited to glutathione antagonists, angiogenesis inhibitors, chemotherapeutic agent(s) and antibodies (e.g., cancer antibodies). The agents described in this invention may be administered simultaneously or sequentially. The separation in time between administrations may be minutes, hours, days or it may be longer.

For example, HE4 inhibitors and ICI inhibitors can be administered before, after, or simultaneously with chemotherapeutic and/or cytotoxic agents such as alkylating agents (e.g., chlorambucil, cyclophosphamide, ccnu, melphalan, procarbazine, thiotepa, bcnu, and busulfan), antimetabolites (e.g., 6-mercaptopurine and 5-fluorouracil), anthracyclines (e.g., daunorubicin, doxorubicin, idarubicin, epirubicin, and mitoxantrone), antitumor antibiotics (e.g., bleomycin), monoclonal antibodies (e.g., alemtuzumab, bevacizumab, cetuximab, gemtuzumab, ibritumomab, panitumumab, rituximab, tositumomab, and trastuzumab), platinums (e.g., cisplatin, oxaliplatin, and carboplatin), plant alkaloids (e.g., vincristine), topoisomerase I or II inhibitors (e.g., irinotecan, topotecan, amsacrine, etoposide, etoposide phosphate, and teniposide), vinca alkaloids (e.g., vincristine, vinblastine, vinorelbine, and vindesine), taxanes (e.g., paclitaxel and docetaxel), epipodophyllotoxins (e.g., etoposide and teniposide), nucleoside analogs, and angiogenesis inhibitors (e.g., Avastin (beracizumab), a humanized monoclonal antibody specific for VEGF-A).

Examples of glutathione antagonists include but are not limited to buthionine sulfoximine, cyclophosphamide, ifosphamide, actinomycin-d and N-(4-hydroxyphenyl) retinamide (4-HPR). Examples of angiogenesis inhibitors include but are not limited to 2-methoxyestradiol(2-ME), AG3340, Angiostatin, antithrombin-III, Anti-VEGF antibody, Batimastat, bevacizumab (Avastin), BMS-275291, CA1, Canstatin, combretastatin, Combretastatin-A4 phosphate, CC-5013, captopril, celecoxib, Dalteparin, EMD121974, Endostatin, Erlotinib, Gefitinib, Genistein, Halofuginone, ID 1, ID3, IM862, Imatinib mesylate, Inducible protein-10, Interferon-alpha, Interleukin-12, Lavendustin-a, LY317615, or AE-941, Marimastat, Mapsin, Medroxyprogesterone acetate, Meth-1, Meth-2, Neovastat, Osteopontin cleaved product, PEX, Pigment epithelium growth factor (PEGF), platelet growth factor 4, prolactin fragment, proliferin-related protein (PRP), PTK787/ZK222584, recombinant human platelet factor-4(rPF4), restin, squalamine, SU5416, SU6668, Suramin, Taxol, Tecogalan, Thalidomide, Tetrathiomolybdate (TM), Thrombospondin, TNP-470, Troponin I, Vasostatin, VEGF1, VEGF-TPvAP and ZD6474. In some embodiment the angiogenesis inhibitor is a VRGF antagonist. The VEGF antagonist may be a VEGF binding molecule. VEGF binding molecule include VEGF antibodies, or antigen binding fragment (s) thereof. One example of a VEGF antagonist is NeXstar.

Examples of categories of chemotherapeutic agents that may be used in any of the methods or agents disclosed herein include, but are not limited to, DNA damaging agents and these include topoisomerase inhibitors (e.g., etoposide, camptothecin, topotecan, irinotecan, teniposide, mitoxantrone), anti-microtubule agents (e.g., vincristine, vinblastine), antimetabolite agents (e.g., cytarabine, methotrexate, hydroxyurea, 5-fluorouracil, flouridine, 6-thioguanine, 6-mercaptompurine, fludarabine, pentostatin, chlorodeoxyadenosine), DNA alkylating agents (e.g., cisplatin, mecholorethamine, cyclophosphamide, ifosphamide, melphalan, chlorambucil, busulfan, thiotepa, carmustine, lomustine, carboplatin, dacarbazine, procarbazine) and DNA strand break inducing agents (e.g., bleomycin, doxorubicin, daunorubicin, idarubicin, mitomycin C).

Chemotherapeutic agents include synthetic, semisynthetic and naturally derived agents. Important chemotherapeutic agents include, but are not limited to, Avicine, Aclarubicin, Acodazole, Acronine, Adozelesin, Adriamycin, aldesleukin, Alitretinoin, AUopurinol sodium, Altretamine, Ambomycin, Ametantrone acetate, Aminoglutethimide, Amsacrine, Anastrazole, Annonaceous Acetogenins, Anthramycin, Asimicin, Asparaginase, asperlin, Azacitidine, azetepa, Azotomycin, batimastat, benzodepa, bexarotene, Bicalutamide, Bisantrene, Bisnafide, Bizelesin, Bleomycin, Brequinar, Bropirimine, Bullatacin, Busulfan, Cabergoline, cactinomycin, calusterone, caracemide, carbetimer, carboplatin, carmustine, carubicin, carzelesin, cedefingol, chlorambucil, celecoxib, cirolemycin, cisplatin, cladribine, crisnatol, cyclophosphamide, cytarabine, dacarbazine, DACA, dactinomycin, Daunorubicin, daunomycin, Decitabine, denileukin, Dexormaplatin, Dezaguanine, Diaziquone, Docetaxel, Doxorubicin, Droloxifene, Dromostalone, Duazomycin, Edatrexate, Eflornithine, Elsamitrucin, Estramustine, Etanidazole, Etoposide, Etoprine, Fadrozole, Fazarabine, Fenretinide, Floxuridine, Fludarabine, Fluorouracil, Flurocitabine, 5-FdUMP, Fosquidone, Fosteuecine, FK-317, FK-973, FR-66979, FR-900482, Gemcitabine, Gemtuzumab, Ozogamicin, Gold Aul 98, Goserelin, Guanacone, Hydroxyurea, Idarubicin, Ilmofosine, Interferon alpha and analogs, Iproplatin, irinotecan, Lanreotide, Letrozole, Leuprolide, Liarozole, Lometrexol, Lomustine, Losoxantrone, masoprocol, Maytansine, Mechlorethamine, Megestrol, Melengestrol, Melphalan, Menogaril, Metoprine, maturedepa, mitindomide, Mitocarcin, Mitogillin, Mitomalacin, Mitomycin, Mitomycin C, Mitosper, Mitotane, Mitoxantrone, Mycophenolic acid, Nocodazole, Nogalamycin, Oprelvekin, ormaplatin, Oxisuran, Paclitaxel, pamidronate, pegaspargase, Peliomycin, Pentamustine, Peplomycin, Perfosfamide, Pipobroman, Piposulfan, Piroxantrone, Plicamycin, Plomestane, Porfimer, Porfiromycin, Prednimustine, procarbazine, Puromycin, Pyrazofurin, Riboprine, Rituximab, Rogletimide, Rolliniastatin, safingol, Samarium, Semustine, Simtrazene, Sparfosate, Sparsomycin, spirogermanium, Spiromustine, Spiroplatin, Squamocin, Squamotacin, streptonigrin, streptozocin, SrC12, Sulphofenur, Talisomycin, Taxane, Toxoid, Tecoglan, Tegafur, teloxantrone, Temoporfin, teniposide, Teroxirone, Testolactone, Thiamiprine, Thiotepa, Thymitaq, Tiazofurin, Tirapazamine, Tomudex, Top-53, Topotecan, Toremixifme, Trastuzumab, Trestolone, triciribine, Triciribine, Trimetrexate, trimetrexate glucuronate, Triptorelin, Tubulozole, uracil mustard, Uredepa, valrubicin, vapreotide, Vinblastine, Vincristine, Vindesine, Vinepidine, Vinglycinate, Vinleurosine, Vinorelbine, Vinrosidine, Vinzolidine, Vorozole, Zeniplatin, Zinostatin, Zorubicin, 2-cholrodeoxyrubicine, 2'-deoxyformycin, 9-aminocamptothecin, raltitrexed, N-propargyl-5,8-didezafolic acid, 2-cholo-2'arabinofluoro-2' deoxyadenosine, 2-cholo-2'-deoxyadenosine, anisomycin, Trichostatin, hPRL-G129R, CEP-751, Linomide, Sulfur mustard, nitrogen mustard, N-methyl-N-nitrosourea, fotemustine, Streptozotocin, dacarbazine, mitozolomide, temozolomide, AZQ, ormaplatin, CI-973, DWA21 14R, JM216, JM335, Bisplatinum, Tomudex, azacitidine, cytrabincine, gemcitabine, 6-mercaptopurine, Hypoxanthine, Teniposide, CPT-11, Doxorubicin, Daunorubicin, Epirubicin, darubicin, losoxantrone, amsacrine, pyrazoloacridine, all trans retinol, 14-hydroxy-retro-retinol, all-trans retinoic acid, N-(4-hydroxyphenyl) retinamide, 13-cisretinoic acid, 3-methyl TTNEB, 9-cisretenoic acid, fludarabine, and 2-Cda.

Other chemotherapeutic agent include: 20-epi1,25-dihydroxyvitamin-D3, 5-ethynyl uracil, abiraterone, aclarubicin, acylfulvene, adecylpenol, adozelesin, aldesleukin, ALL-TK antagonists, altretamine, ambumastine, amidox, amifostine, amino levulinic acid, anagrelide, anastrozole, andrographolide, angiogenesis inhibitors, antagonist D, antagonists D, antarelix, anti-dorsalizing morphogenetic protein-1, antiandrogen, antiestrogen, antineoplastone, antisense oligonucleotides, aphidicolin, apoptosis gene modulators, apoptosis regulators, apurinic acid, ara-cdp-dl-PTBA, arginine aminase, asulacrine, atamestine, atrimustine, axinamastine 1 and axinamastine 2, axinamastine 3, azasetron, azatoxin, azatyrosine, baccatin III derivatives, balanol, BCR/ABL antagonist, benzochlorins, benzoylsaurosporine, beta lactam derivatives, beta-alethine.

Perillyl alcohol, phenozenomyein, phenyl acetate, phosphatase inhibitors, picibanil, pilocarbine and salts or analogs thereof, pirarubicin, piritrexim, placetin A, placetin B, plasminogen activator inhibitor, platinum complex, phenyl ethyl isothiocyanate and analogs thereof, platinum compounds, platinum triamine complex, podophylotoxin, porfimer sodium, porphyromycin, propyl bis acridones, prostaglnadins J2, protease inhibitors, protein A based immune modulators, PKC inhibitors, microalgal, protein tyrosine phosphatase inhibitors, purine nucleoside phosphorylase inhibitors, purpurins, pyrazoloacridines, pyridoxylated hemoglobin polyoxyethylene conjugate, raf antagonists, raltitrexed, ramosetron, ras farnesyl protein tranferase inhibitors, rasinhibitors, ras-GAP inhibitors, ratellitptine demethylated, Rhenium Re 186 etidronate, rhizoxine, ribozyme, RII retinide, rogletimide, rosagliatazone and analogs and derivatives thereof, rohitukine, romurtide, roquinimex, rubiginone B1, ruboxyl, safingol, saintopin, SarCNU, sarcophytol A, sargrmostim, sdi 1 mimetics, semustine, senescence derived inhibitor 1, sense oligonucleotide, signal transduction inhibitors, signal transduction modulators, single chain antigen binding protein, sizofiran, sobuzoxane, sodium borocaptate, sodium phenyl acetate, solverol, somatomedin binding protein, sonermin, sparfosic acid, spicamycin D, spiromustin, splenopentine, spongistatin 1, squalamine, stem cell inhibitor, stem cell division inhibitor, stipiamide, stromelysin, sulfinosine, superactive vasoactive intestinal peptide antagonists, suradista, siramin, swainsonine, synthetic glycosaminoglycans, tallimustine, tamoxifen methiodide, tauromustine, tazarotene, tacogalan sodium, tegafur, tellurapyrilium, telomerase inhibitors, temoporfin, tmeozolomide, teniposide, tetrachlorodecaoxide, tetrazomine, thaliblastine, thalidomide, thiocoraline, thrombopoetin and mimetics thereof, thymalfasin, thymopoetin receptor agonist, thymotrinan, thyroid stimulating harmone, tin ethyl etiopurpin, tirapazamine, titanocene and salts thereof, topotecan, topsentin, toremifene, totipotent stem cell factors, translation inhibitors, tretinoin, triacetyluridine, tricribine, trimetrexate, triptorelin, tropisetron, turosteride, tyrosine kinase inhibitors, tyrphostins, UBC inhibitors, ubenimex, urogenital sinus derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozol, zanoterone, zeniplatin, zilascorb and zinostatin.

Other chemotherapeutic agents include: antiproliferative agents (e.g., piritrexim isothiocyanate), antiprostatic hypertrophy agents (sitogluside), Benign prostatic hyperplasia therapy agents (e.g., tomsulosine, RBX2258), prostate growth inhibitory agents (pentomone) and radioactive agents: Fibrinogen 1125, fludeoxyglucose F18, Flurodopa F18, Insulin 1125, Iobenguane 1123, Iodipamide sodium 1131, Iodoantipyrine 1131, Iodocholesterol 1131, Iodopyracet 1125, Iofetamine HCL 1123, Iomethin 1131, Iomethin 1131, Iothalamate sodium 1125, Iothalamate 1131, Iotyrosine 1131, Liothyronine 1125, Merosproprol Hgl 97, Methyl ioodobenzo guanine (MIBG-I131 or MIBGI 123) selenomethionine Se75, Technetium Tc99m furifosmin, technetium Tc99m gluceptate, Tc99m Biscisate, Tc99m disofenin, TC99m gluceptate, Tc99m lidofenin, Tc99m mebrofenin, Tc99m medronate and sodium salts thereof, Tc99m mertiatide, Tc99m oxidronate, Tc99m pentetate and salts thereof, Tc99m sestambi, Tc99m siboroxime, Tc99m succimer, Tc99m sulfur colloid, Tc 99m teboroxime, Tc 99m Tetrofosmin, Tc99m Tiatide, Thyroxine 1125, Thyroxine 1131, Tolpovidone 1131, Triolein 1125 and Treoline 1125, and Treoline 131, MIBG-I123 and MIBG 1131 are especially preferred chemotherapeutic agents for co-administration with the nitrofuran containing pharmaceutical composition of invention.

Another category of chemotherapeutic agents are anticancer supplementary potentiating agents, e.g., antidepressant drugs (Imipramine, desipramine, amitriptyline, clomipramine, trimipramine, doxepin, nortriptyline, protriptyline, amoxapine, and maprotiline), or no-trycyclic anti-depressant drugs (sertraline, trazodone and citalopram), Ca++ antagonists (verapamil, nifedipine, nitrendipine and caroverine), calmodulin inhibitors (prenylamine, trifluoperazine and clomipramine), Amphotericin B, Triparanol analogs (e.g., Tamoxifen), antiarrhythmic drugs (e.g., quinidine), antihypertensive drugs (e.g., reserpine), thiol depleters (e.g., buthionine and sulfoximine) and multiple drug resistance reducing agents such as Cremophor EL.

Other chemotherapeutic agents include: annoceous acetogenins, ascimicin, rolliniastatin, guanocone, squamocin, bullatacin, squamotacin, taxanes, baccatin. One important class of chemotherapeutic agents are taxanes (paclitaxel and docetaxel). The compounds of this invention in combination with tamoxifen and aromatase inhibitors arimidex (e.g., anastrazole) are particularly useful for treatment of cancers.

Another important class of molecules that is used to treat cancer in combination with compounds and methods of this invention include but are not limited to anti-CD20 mAB, rituximab, Rituxan, Tositumoman, Bexxar, anti-HER2, Trastuzumab, Herceptin, MDX20, antiCA125 mAB, antiHE4 mAB, oregovomab mAB, B43.13 mAB, Ovarex, Breva-REX, AR54, GivaRex, ProstaRex mAB, MDX447, gemtuzumab ozoggamycin, Mylotarg, CMA-676, anti-CD33 mAB, anti-tissue factor protein, Sunol, IOR-C5, C5, anti-EGFR mAB, anti-IFR1R mAB, MDX-447, anti-17-1A mAB, edrecolomab mAB, Panorex, anti-CD20 mAB, (Y-90 lebelled), Ibritumomab Tiuxetan (IDEC-Y2B8), Zevalin, anti-Idiotypic mAB.

IV. Kits

Provided herein are kits for measuring the expression levels of HE4 and one or more ICIs or for inhibiting the expression levels of the same, respectively. These kits can include, for example, one or more binding agents (such as antibodies or fragments thereof) capable of specifically binding to HE4 and one or more ICI proteins or fragments thereof. For example, any one of the one or more binding agents may be an antibody, aptamer, photoaptamer, protein, peptide, peptidomimetic or a small molecule. In one embodiment, any one of HE4 and one or more ICI proteins may be advantageously immobilized on a solid phase or support. The kits may also include reagents and means for measuring the quantity of HE4 and one or more ICI nucleic acids, proteins, or fragments thereof. For example, the kits can employ immunoassays, mass spectrometry analysis technology, or chromatographic technology, or a combination of the technologies.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention can be further understood by reference to the following examples, which are provided by way of illustration and are not meant to be limiting.

EXAMPLES

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition, Cold Spring Harbor Laboratory Press, Cold Spring Harbor, N.Y. (Greenfield, ed., 2014), Beaucage et al. eds., *Current Protocols in Nucleic Acid Chemistry*, John Wiley & Sons, Inc., New York, 2000, (including supplements through 2014) and *Gene Transfer and Expression in Mammalian Cells* (Makrides, ed., Elsevier Sciences B.V., Amsterdam, 2003).

Example 1: Correlation of HE4 Levels with CD8+ T-cell Infiltration in Ovarian Tumors Materials and Methods:

The relative expression of HE4 and population of CD8+ T cells in high HE4 expressor versus low HE4 overexpressor patients was measured, and the results from analysis of immunohistochemical stainings that were performed on paraffin-embedded slides tumor specimens (thickness 5 μm) is shown in FIG. 1. Tissue sections were deparaffinized and rehydrated with serial ethanol dilutions of 100, 95 and 70%. Heat-induced antigen retrieval was then performed using DAKO Antigen Retrieval Solution for 20 minutes. Tissue sections were blocked with Normal donkey or horse Blocking Serum (obtained from Vector Laboratories) for 60 minutes at room temp before incubating with primary antibodies for HE4 (obtained from Origene, MD, USA) prepared in a 1:50 dilution and CD8 antibody prepared in a 1:50 dilution (obtained from Origene, MD, USA) in a humidified chamber overnight at 4° C. Secondary antibodies were applied and incubated for 60 minutes for 1 hour at room temperature in the dark.

The secondary antibodies used in this study included DyLight 594 goat anti-rabbit IgG, Jackson ImmunoResearch Laboratories, INC. and Alexa Fluor 594 goat anti-mouse IgG at 1:500, Invitrogen. Vectashield media with DAPI (obtained from Vector Laboratories) was used to mount cover-slips for further analysis. Sixteen bit images were acquired with a Nikon E800 microscope (Nikon Inc. Mellville N.Y.) using a 40× PlanApo objective. A Spot II digital camera (Diagnostic Instruments, Sterling Heights Mich.) acquired the images. The camera's built-in green filter was used to increase image contrast. Camera settings were based on the brightest slide. All subsequent images were acquired with the same settings. CD+ T-cells were manually counted per $\mu m^2$ area of the tumor specimens. Image processing and analysis was performed using iVision (BioVision Technologies, version 10.4.11, Exton, Pa.) image analysis software. Positive staining was defined through intensity thresholding and integrated optical density (IOD) was calculated by examining the thresholded area multiplied by the mean. All measurements were performed in pixels. Statistical analysis was done using an online statistical calculator. Student's t-test was performed for calculating the CD8+ tumor infiltrating lymphocyte count compared to HE4 level.

Figure 2:
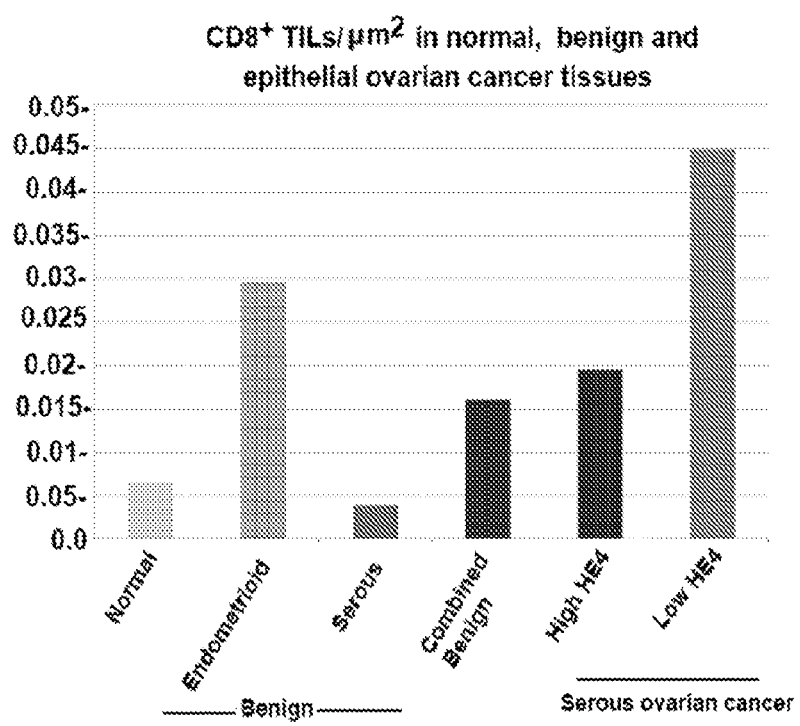
FIG. 2 depicts a bar graph showing HE4 levels correlate with reduced CD8+ T cell infiltration in ovarian tumors. Normal, serous ovarian cancer tumors, benign and tissues such as endometrioid and were stained for HE4 and CD8+ T cell-lymphocytes. HE4>400 pM Tumors were classified as high expressors and HE4<400 pM were classified as low HE4 expressors. CD8+ T cells were counted per μM² area in tumors of each group.

Results:

In the analysis of the stained samples of Ovarian cancer tumors and benign tissues stained for HE4 and CD8+ T cell-lymphocytes, HE4>400 pM Tumors were classified as high expressors and HE4<400 pM were classified as low expressors. CD8+ T cells were counted per $\mu m^2$ area in tumors of each group. The statistical correlation of intratumoral HE4 with number of CD8+ T-cell lymphocytes in the tumor specimen was analyzed and the results are shown in FIG. 1 and FIG. 2. Serous carcinoma with high serum HE4 exhibit statistically lower number of CD8+ T-cell lymphocytes (p=0.003), indicating that HE4 levels correlate with reduced CD8+ T-cell infiltration in ovarian tumors.

Example 2: Colocalization of HE4 and PD-L1 in Normal, Benign, and Serous Ovarian Tumors Materials and Methods:

Co-localization of HE4 with PD-L1 in ovarian normal, benign, and serous cancer tissues was determined by immunohistochemical stainings that were performed on paraffin-embedded slides tumor specimens with thicknesses of 5 μm. Tissue sections were deparaffinized and rehydrated with serial ethanol dilutions of 100%, 95%, and 70%. Heat-induced antigen retrieval was then performed using DAKO Antigen Retrieval Solution for 20 minutes. Tissue sections were blocked with Normal horse Blocking Serum (obtained from Vector Laboratories) for 60 minutes at room temperature before incubating with primary antibodies for HE4 in a humidified chamber overnight at 4° C. The primary antibodies used included those obtained from Origene, MD, USA, used in a 1:50 dilution and PD-L1 in a 1:50 dilution, obtained from Origene, MD, USA. Secondary antibodies (e.g., DyLight 594 goat anti-rabbit IgG, Jackson ImmunoResearch Laboratories, INC. and Alexa Fluor 594 goat anti-mouse IgG at 1:500 dilution, obtained from Invitrogen) were applied and incubated for 60 minutes (e.g. for 1 hour) at room temperature in the dark. Vectashield media with DAN (Vector Laboratories) was used to mount cover-slips for further analysis. Sixteen bit images were acquired with a Nikon E800 microscope (Nikon Inc. Melville N.Y.) using a 40× PlanApo objective. The images were acquired using A Spot 11 digital camera (obtained from Diagnostic Instruments, Sterling Heights Mich.). The camera's built-in green filter was used to increase image contrast. Camera settings were based on the brightest slide. All subsequent images were acquired with the same settings. Image processing and analysis was performed using iVision (BioVision Technologies, version 10.4.11, Exton, Pa.) image analysis software. Positive staining was defined through intensity thresholding and integrated optical density (IOD) was calculated by examining the thresholded area multiplied by the mean. All measurements were performed in pixels. Confocal images were acquired with a Nikon C1si confocal (Nikon Inc. Mellville N.Y.) using diode lasers with wavelengths of 402 nm, 488 nm, and 561 nm. Serial optical sections were performed with EZ-C1 computer software (Nikon Inc. Mellville, N.Y.). Z series sections were collected at 0.3 μm with a 40× PlanApo lens and a scan zoom of 2. The gain settings were based on the brightest slide and kept constant between specimens. Deconvolution and projections were done in Elements (Nikon Inc. Mellville, N.Y.) computer software. Co-localization was considered positive when Pearson coefficient was found to be more than 0.9.

Figure 3:
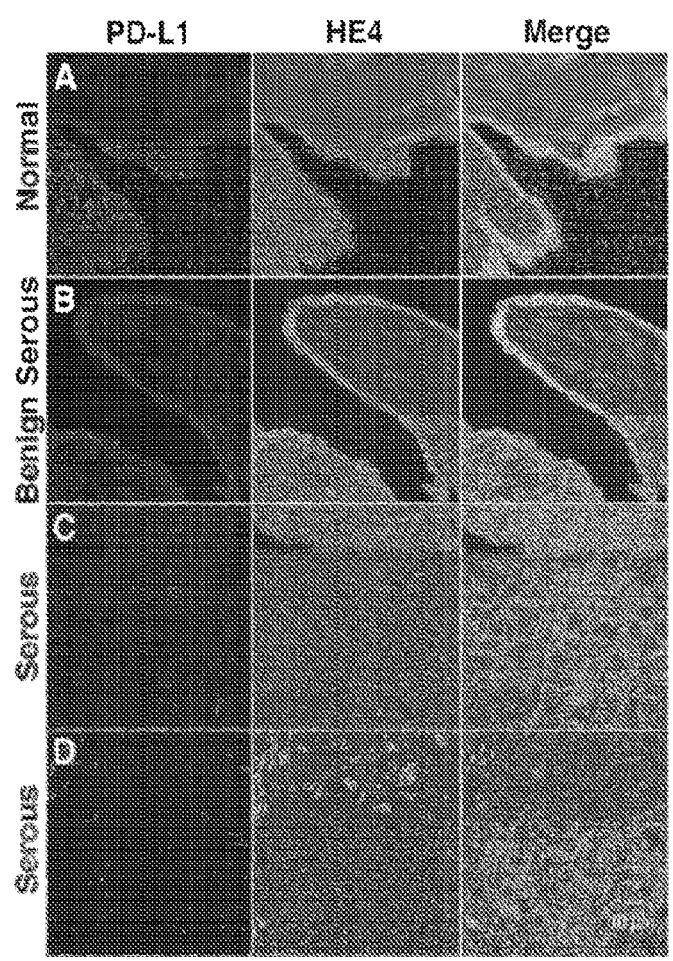
FIG. 3 is a fluorescent micrograph depicting HE4 and PD-L1 colocalize in normal, benign and serous ovarian tumors. Ovarian cancer tumors and benign tissues were stained for HE4 and PD-L1 expression using corresponding primary and appropriate secondary antibodies. The collocalization was detected by confocal microscopy and Pearson Coefficient more than 0.9 was considered as positive co-localization.

Results:

FIG. 3 shows that HE4 and PD-L1 co-localize in normal, benign, and serous ovarian tumors when stained for HE4 and PD-L1 expression using corresponding primary and appropriate secondary antibodies, as described above. The co-localization was detected by confocal microscopy and Pearson Coefficient more than 0.9 was considered as positive co-localization.

Example 3: Overexpression of HE4 and PD-L1 Expression in Serous Ovarian Cancer Tissues Materials and Methods:

Ovarian cancer tumors tissues were stained for HE4 and PD-L1 expression using corresponding primary and appropriate secondary antibodies. Expression levels of HE4 and PD-L1 were measured by calculating Integrated optical density (IOD) units of HE4 and PD-L1 intensity of expression in 6-7 arbitrarily chosen fields in tumor specimens. Paraffin-embedded slides tumor specimens of thickness 5 μm were stained immunohistochemically. Tissue sections were deparaffinized and rehydrated with serial ethanol dilutions of 100%, 95%, and 70%. Heat-induced antigen retrieval was then performed using DAKO Antigen Retrieval Solution for 20 minutes. Tissue sections were blocked with Normal horse Blocking Serum (obtained from Vector Laboratories) for 60 minutes at room temperature before incubating with primary antibodies for HE4 at a 1:50 dilution (obtained from Origene, MD, USA) and PD-L1 at a 1:50 dilution (obtained from Origene, MD, USA) in a humidified chamber overnight at 4° C. Secondary antibodies were applied and incubated for 60 minutes (e.g. for 1 hour) at room temperature in the dark. The secondary antibodies used included DyLight 594 goat anti-rabbit IgG, Jackson ImmunoResearch Laboratories, INC. and Alexa Fluor 594 goat anti-mouse IgG at a dilution of 1:500, obtained from Invitrogen. Vectashield media with DAPI (obtained from Vector Laboratories) was used to mount cover-slips for further analysis. Sixteen bit images were acquired with a Nikon E800 microscope (Nikon Inc. Mayville N.Y.) using a 40× PlanApo objective. Images were acquired using a Spot II digital camera (Diagnostic Instruments, Sterling Heights Mich.). The camera's built-in green filter was used to increase image contrast. Camera settings were based on the brightest slide. All subsequent images were acquired with the same settings. Image processing and analysis was performed using iVision (BioVision Technologies, version 10.4.11, Exton, Pa.) image analysis software. Positive staining was defined through intensity thresholding and integrated optical density (IOD) was calculated by examining the thresholded area multiplied by the mean. All measurements were performed in pixels. Verification of the association of HE4 staining to PDL1 staining. P<0.05 was considered as significant was done using the one-sided t-test.

Figure 4:
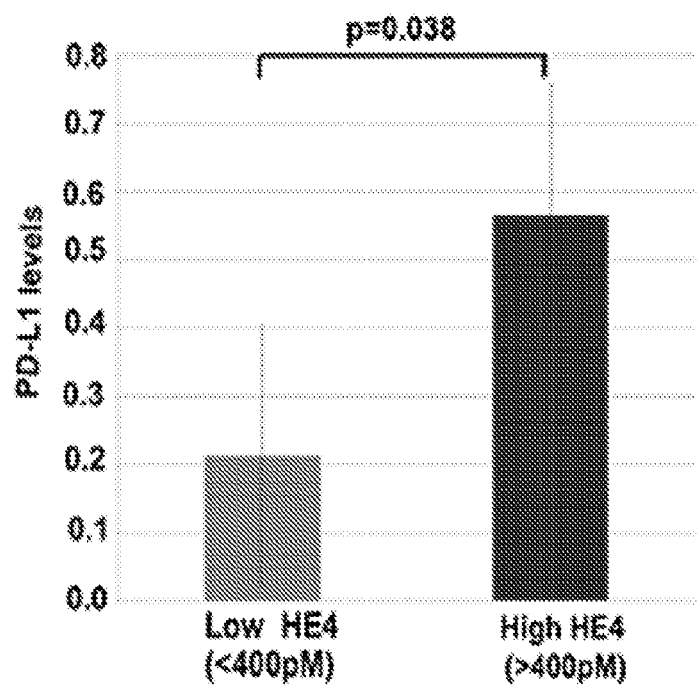
FIG. 4 is a bar graph depicting HE4 overexpression leads to significant overexpression of PD-L1 colocalize in serous ovarian tumor tissues. Ovarian cancer tumors tissues were stained for HE4 and PD-L1 expression using corresponding primary and appropriate secondary antibodies. Expression levels of HE4 and PD-L1 were measured by calculating Integrated optical density (IOD) units of HE4 and PD-L1. HE4 levels were observed that correlated statistically with PD-L1 levels in the tumors.

Results:

HE4 overexpression leads to significant overexpression of PD-L1 co-localized in serous ovarian tumor tissues, as shown in FIG. 4. Ovarian cancer tumors tissues were stained for HE4 and PD-L1 expression using corresponding primary and appropriate secondary antibodies, as described above. Expression levels of HE4 and PD-L1 calculated using integrated optical density (IOD) units of HE4 and PD-L1 showed HE4 levels correlated statistically with PD-L1 levels in the tumors.

Example 4: Antisense Inhibition of HE4 Correlation to PD-L1 Expression in Xenograft Ovarian Cancer Tissues Materials and Methods:

Four to six week-old immunodeficient nude mice were maintained at a temperature of 22±1'C and a relative humidity of 55±5%, with a 12 hour light/dark cycle. The mice used in this example were NU/NU; strain code 088/homozygous, obtained from Charles River Laboratories, Wilmington, Mass. The inoculation of the mice included culturing SKOV-3 cells to 80% confluence, washing in PBS twice, and harvesting the cells by trypsination. The harvested cells were then pooled in complete medium, washed in PBS twice, and $2\times10^6$ cells/inoculate were suspended in 0.1 ml of matrigel. This cell suspension was used to inoculate each mouse subcutaneously in the flank. Mice with developing tumors after two weeks were randomly assigned to experimental groups. Mice (n=7 each) were treated intraperitoneally every day with either vehicle control or HE4 antisense-1 (RR-1) (7 mg/kg bwt, 5× week) or scrambled (7 mg/kg bwt, 5× week) for 10 days. Mice were weighed and tumor site calculated using a caliper every 5 days. The Kaplan-Meier method was used to estimate survival curves. The xenograft tissues were harvested after euthanasia and fixed in paraformaldehyde and embedded in paraffin. The slides of 5 μm were stained for the expression of PD-L1 using the primary antibody (obtained from Origene, MD, USA) and corresponding fluorescence linked secondary and images were recorded as described previously (see Moore et al, Plos One, 2012).

Figure 5:
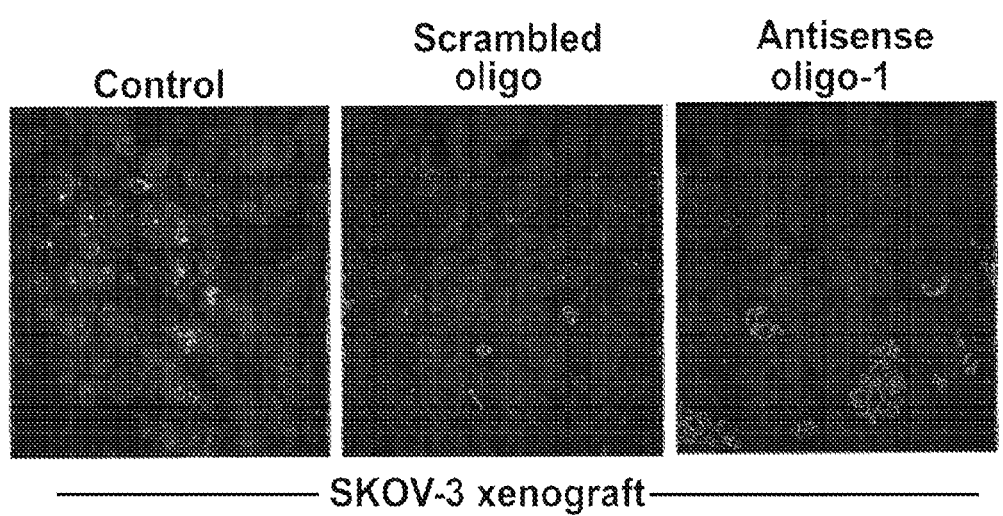
FIG. 5 is a fluorescent micrograph depicting HE4 targeting antisense phosphorothio-oligos (PTOS) inhibit PD-L1 expression in xenograft ovarian tumor tissues. HE4 targeting antisense (5 mg/kg, 5 times/week, IP) PTOs downregulate PD-L1 levels in serous ovarian cancer cell-line based xenograft in animals.

Results:

HE4 targeting antisense phosphorothio-oligos (PTOS) inhibit PD-L1 expression in xenograft ovarian tumor tissues, as determined from stains of tumors grown in mice and stained for the expression of PD-L1. FIG. 5 shows HE4 targeting antisense (5 mg/kg, 5 times/week, IP) PTOs downregulate PD-L1 levels in serous ovarian cancer cell-line based xenograft in animals.

Example 5: HE4 Targeting Third Generation Antisense Locked Nucleic Acid (LNA) Oligos and PD-L1 Expression in Serous Ovarian Tumor Materials and Methods:

SKOV-3 human ovary adenocarcinoma cells were purchased from American Tissue Culture Collection (ATCC) (world wide web.atcc.org) and maintained in DMEM media (soured from Invitrogen Inc.) supplemented with fetal bovine serum (10%) and antibiotics (1%). High HE4 overexpressing ovarian cancer cell-line clones SKOV-3 C1 were developed, as described previously (see Moore et al, Sci Rep 2014). SKOV-3 C1 cells were seeded in a 6-well petri-dishes containing 1 mL of the complete DMEM media, with approximately 400,000 cells per well. The cells were then allowed to adhere and incubate overnight. Media was replaced with antibiotic free transfection media containing vehicle, Lipofectamine (5 μL) alone or adduct of lipofectamine (5 μL)+HE4 antisense oligo (50 nM), lipofectamine (5 μL)+ scrambled oligo (50 nM) or scrambled oligos (50 nM) alone and the cells were incubated for 48 hours. Media was collected and stored at −20° C. for future studies. Preparation of cell lysates, PAGE and immunoblotting with appropriate antibodies purchased from Origene (MD, USA) was carried out as described (Moore et al, Plos One, 2012 and references cited therein). Briefly, protein concentration of the remaining supernatant of the cell lysate was quantitated (BioRad protein estimation kit, Hercules, Calif.) and Western blotting was carried out. Samples were boiled in the presence of 5×SDS-PAGE sample buffer and 50 μg total cellular protein/lane were separated on 12% SDS-polyacrylamide gels and blotted onto PVDF membranes. The blots were blocked with 5% nonfat dry milk in PBST for 1 hour at room temperature and incubated overnight at 4° C. with the antibodies against HE4 and PD-L1. After washing in PBST the blots were incubated with secondary antibody (peroxidase-conjugated antibodies; Amersham-Pharmacia Biotech, Piscataway, N.J.). The bands were visualized using horseradish peroxidase-conjugated secondary antibodies (Amersham-Pharmacia Biotech, Piscataway, N.J.) and documented by autoradiography (F-B.810 Film, Phenix, Hayward, Calif.).

Figure 6:
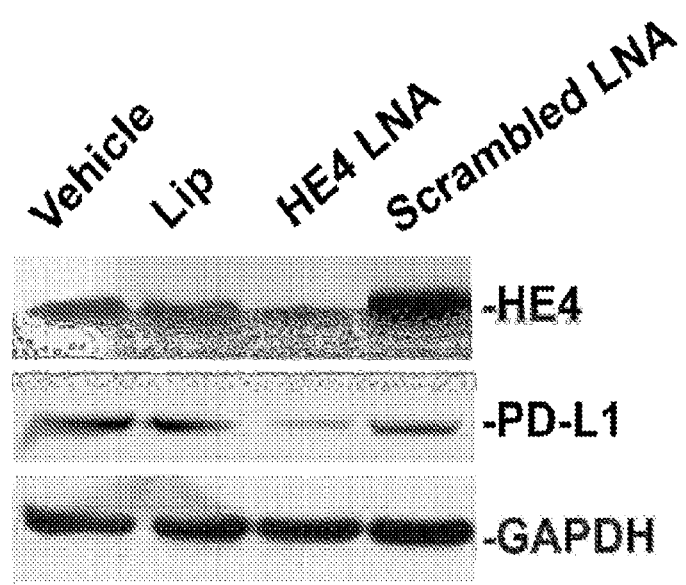
FIG. 6 is an image depicting HE4 targeting third generation antisense locked nucleic acid (LNA) oligos inhibit PD-L1 expression in serous ovarian tumor tissues. HE4 targeting antisense LNAs (50 nM) treatment of 48 hours downregulated expression of HE4 and PD-L1 levels in serous ovarian cancer cell-line SKOV-3. The sequence of the negative control, Antisense-1 and Antisense-2 has been described below.

Results:

HE4 targeting third generation antisense locked nucleic acid (LNA) oligos inhibit PD-L1 expression in serous ovarian tumor tissues as determined by Western blotting, as shown in FIG. 6. HE4 targeting antisense LNAs (50 nM) treatment of 48 hours downregulated expression of HE4 and PD-L1 levels in serous ovarian cancer cell-line SKOV-3. The sequence of the negative control, Antisense-1, and Antisense-2 is summarized in the table below:

| Sequence of Locked Nucleic Acid (LNA) LongRNA GAPmer Oligos Targeting HE4 | |
|---|---|
| Sequence-1: Negative control: | (SEQ ID NO: 3) |
| 5'-3': AACACGTCTATACGC | |
| HE4-antisense sequence-1: | (SEQ ID NO: 1) |
| 5'-3': TTGCTGAAAGTGGTTA | |
| HE4-antisense sequence-2: | (SEQ ID NO: 2) |
| 5'-3': AGAGTCCCGAAAAAGG | |

Example 6: Recombinant HE4 Activated PD-1 in Donor Human PMBCs

Materials and Methods:

Ficoll-Paque density gradient centrifugation was used to isolate PBMC from heparinized venous blood. Unfractionated PBMC were suspended in serum free RPMI1640 medium. Then the cells were incubated with recombinant HE4 (5.4 nM) or vehicle for 6 hours. TRIzol reagent was used to isolate the total RNA, and the first strand cDNA was made by SuperScript III reverse transcriptase. RT-PCR for the cDNA was done with PD-1 or GAPDH (internal control) gene specific primers. The primer sequences used for PD-1 are F-GCCTGTGTTCTCTGTGGACT (SEQ ID NO:4); R-ACAATGGTGGCATACTCCGT SEQ ID NO:5). The primer sequences used for internal control (GAPDH) are F-AATCCCATCACCATCTTCC SEQ ID NO:6); R-gTC-CTTCCACgATACCAAAg SEQ ID NO:7).

Figure 7:
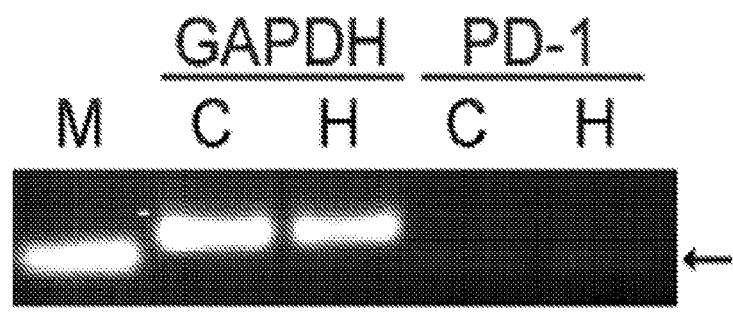
FIG. 7 is an image depicting exogenous recombinant HE4 activates PD-1 expression in donor PMBCs. hHE4 (5.4 nM) was added to PMBCs and the expression of PD-1 and GAPDH as internal control was measured by rt-PCR. The calculation of PD-1/GAPDH ratio suggests strong increase (77.7%) in PD-1 expression within 6 hours. PMBCs contain ~75% of CD8+ and CD4+ positive T cells.

Results:

Exogenous recombinant HE4 activates PD-1 expression in donor PMBCs, as seen in FIG. 7. HE4 (5.4 nM) was added to PMBCs and the expression of PD-1 and GAPDH as internal control was measured by rt-PCR, as described above. The calculation of PD-1/GAPDH ratio suggests strong increase (77.7%) in PD-1 expression within 6 hours. PMBCs contain ~75% of CD8+ and CD4+ positive T-cells.

Example 7: Correlation of Changes in Tumor Size and Murine Body Mass with Application of HE4 Antisense Locked Nucleic Acid (LNA) Oligos Materials and Methods:

Four to six week-old immunodeficient nude mice were maintained at a temperature of ~22° C. and a relative humidity of ~55%, with a 12 hour light/dark cycle. The mice used were NU/NU; strain code 088/homozygous, obtained from Charles River Laboratories, Wilmington, Mass. The inoculation of the mice began with culturing SKOV-3 cells to 80% confluence, washing the SKOV-3 cells in PBS twice, and harvesting the cells by trypsination. The harvested cells were then pooled in complete medium, washed in PBS twice, and 2×10$^6$ cells/inoculate were suspended in 0.1 ml of matrigel. This cell suspension was used to inoculate the mice subcutaneously in the flank of each mouse. Mice with developing tumors after two weeks were randomly assigned to experimental groups. Mice were treated intraperitoneally with either vehicle control (control group; 7 animals) or Antisense-1 (7 mg/kg bwt) or scrambled PTO (7 mg/kg bwt) for 7 days. In another arm mice were treated with cisplatin (10 mg/kg, once a week), or scrambled PTO (7 mg/kg, 5 times/week)+ cisplatin (10 mg/kg, IP, once a week) or Antisense-1 (7 mg/kg, IP, once a week)+ Cisplatin (10 mg/kg, IP, once a week). Mice were weighed and tumor size was measured using a digital caliper every 3 days. The change in the tumor size was calculated in % units, as shown in FIG. 8.

Figure 8:
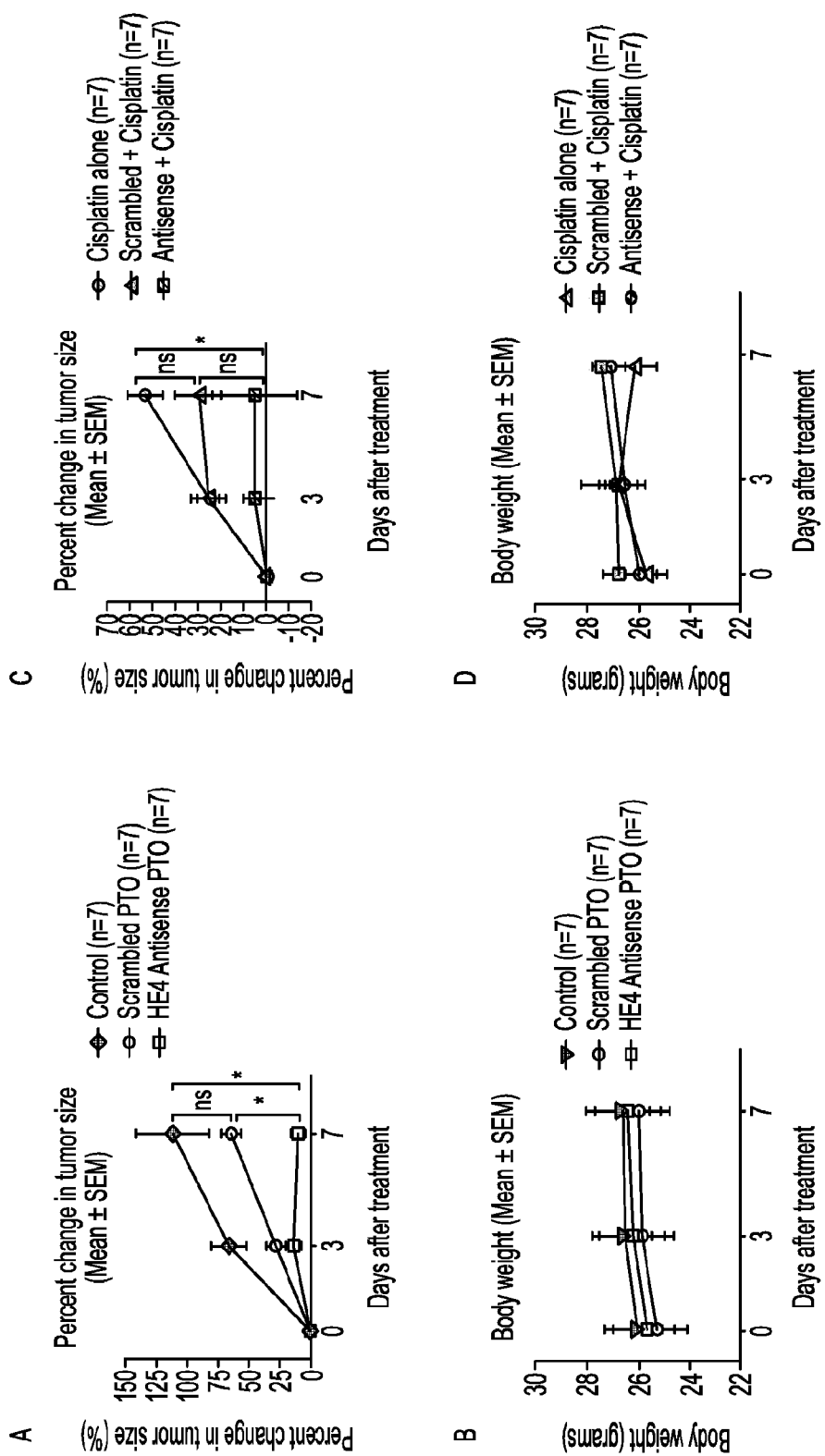
FIG. 8 is a series of graphs depicting antisense targeting of HE4 decreases tumor growth in a cisplatin-resistant murine model of ovarian cancer. Percent change in tumor size following (A) antisense treatment or (C) antisense+Cisplatin. (B) and (D): Changes in murine body weight (Mean+/−SEM).

Results:

FIG. 8 shows minimal or no percent change in tumor size in mice that were treated with either Antisense-1 or Antisense-1+ Cisplatin. Tumors in the control group of mice or those treated with scrambled PTO, cisplatin alone, or scrambled PTO+ cisplatin showed an increase in tumor size at least initially. The data does not show significant weight loss of any of the mice during treatment. This indicates some ability of applied HE4 antisense locked nucleic acid (LNA) oligos to treat cisplatin-resistant tumors in a murine model.

Example 8: MetC7 Treatment Inhibits PD-L1 Expression in Ovarian and Medulloblastoma Cancer Cell Lines This Example shows that PD-L1 co-localizes with the vitamin D receptor (VDR) in ovarian cancer cell lines and that treatment of ovarian cancer cell lines with the specific VDR antagonist MeTC7 downregulates PD-L1 expression.

Materials and Methods:

Co-localization of VDR and PD-L1 was performed following the method in the Examples above. To determine the expression level of PD-L1 after MeTC7 treatment (125 nM), 10000 cells/well of SKOV-3, OVCAR-8 human ovarian carcinoma cells, IGROV-1 human ovarian carcinoma cells, and ID-8 murine ovarian cancer cells were seeded in an 8 well slide chamber (Nunc) and allowed to adhere overnight in FBS supplemented DMEM media. After 18 hours, the media was removed and the cells were treated with vehicle or MeTC7 supplemented DMEM serum free media for 4-6 hours. Cells maintained in DMEM medium were fixed with formalin solution for 15 mins, washed with PBST solution and blocked with Donkey serum 5% in PBST for 30 minutes. Cells were carefully washed and stained with PD-L1 primary antibody overnight in PBST. The cells were washed and stained with corresponding fluorescence linked secondary antibody for 1 hour. Cells were washed repeatedly with PBST (200 µL) five times. Casing on the chambers were removed and DAPI was applied in a mounting medium and images were recorded using an epi or confocal microscopy.

Figure 9A:
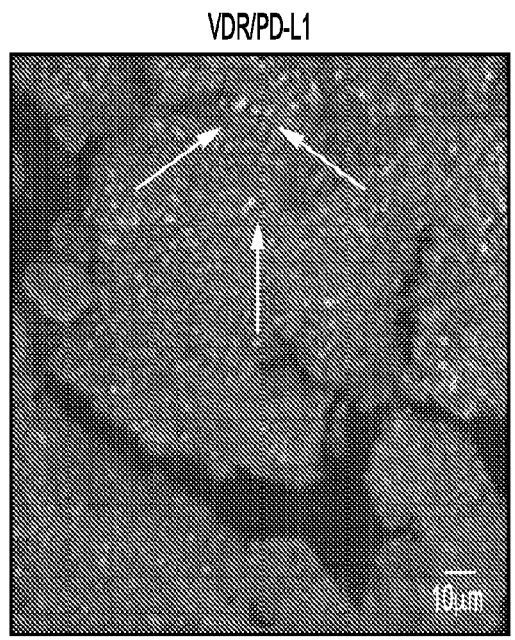
FIG. 9A is a fluorescent micrograph depicting co-localization of the vitamin D receptor (VDR) and PD-L1.
Figure 9B:
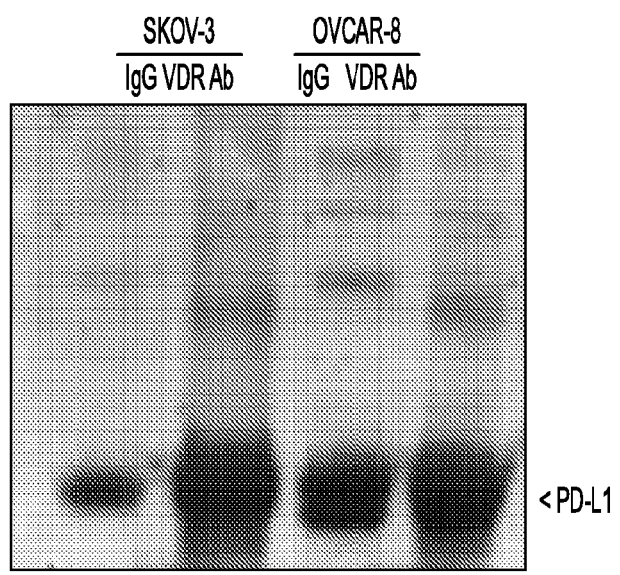
FIG. 9B is an image depicting the immunoprecipitation of PD-L1 using an antibody to the VDR in SKOV-3 and OVCAR-8 ovarian cancer cell lines.
Figure 10:
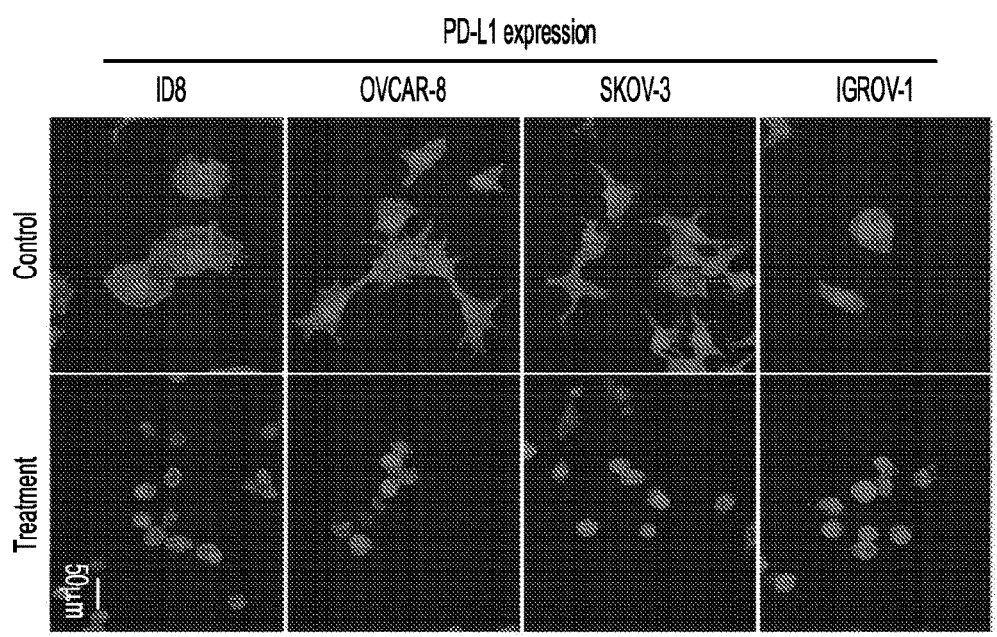
FIG. 10 is a fluorescent micrograph depicting the effects of treating ID8, OVCAR-8, SKOV-3 and OGROV-1 ovarian cancer cells with the small molecule VDR antagonist MeTC7.

Results:

Fluorescent labeling of tissues derived from subjects with ovarian cancer were sectioned and fluorescently labeled with antibodies directed to VDR and PD-L1. Both of these proteins were observed to co-localize in ovarian cancer tissue (FIG. 9A). Further, an antibody to the VDR was also able to immunoprecipitate PD-L1 in two separate ovarian cancer cell lines (FIG. 9B). Four separate ovarian cancer cell lines were then treated with the specific BDR antagonist MeTC7. In all four cell lines, MeTC7 treatment was observed to down regulate D-L1 expression (FIG. 10).

Figure 11:
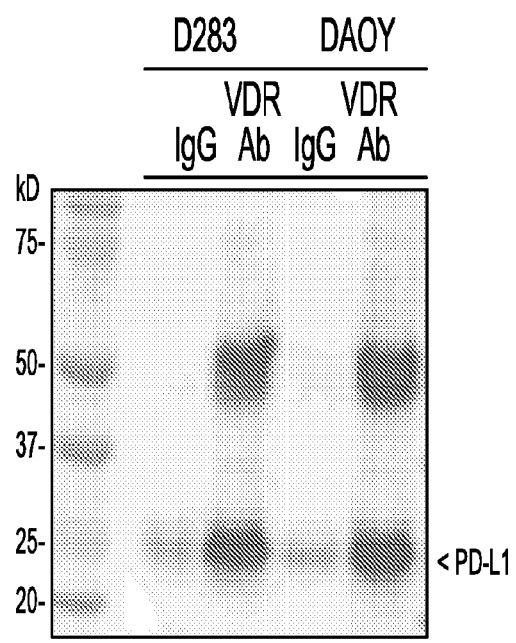
FIG. 11 is an image depicting the immunoprecipitation of PD-L1 using an antibody to the VDR in D283 and DAOY medulloblastoma cell lines.
Figure 12:
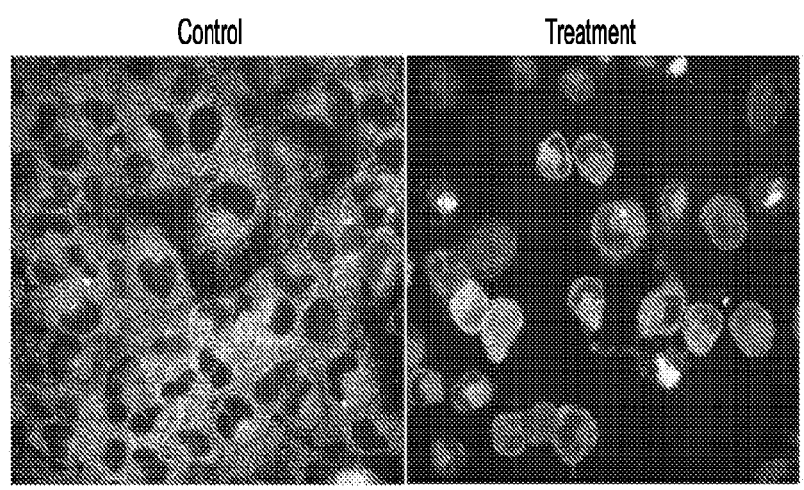
FIG. 12 is a fluorescent micrograph depicting the effects of MeTC7 (125 nM) treatment on immune checkpoint PD-L1 expression in DAOY (human) medulloblastoma cells. Treated/naïve DAOY cells were analyzed by spinning disk confocal microscopy after staining with PD-L1 primary and suitable secondary antibodies.

Similar experiments were performed using medulloblastoma cell lines. As was observed with ovarian cancer cells, an antibody to the VDR immunoprecipitated PD-L1 in two medulloblastoma-derived cell lines (FIG. 11). Moreover, in DAOY medulluoblastoma cells, MeTC7 treatment reduced PD-L1 expression (FIG. 12). However, a similar effect was not found when these experiments were performed on melanoma cells.

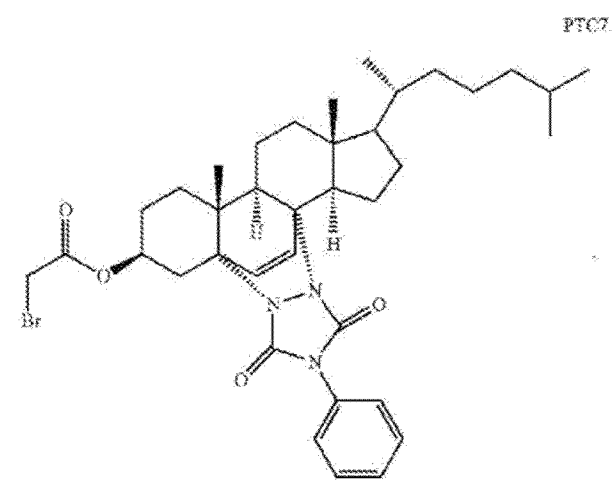

The invention claimed is:

1. A method of suppressing tumor cell proliferation in a subject comprising: concurrently or sequentially inhibiting
   (a) the activity or level of human epididymal secretory protein E4 (HE4) in said tumor cell; and
   (b) the activity or level of one or more immune checkpoint inhibitors (ICIs) in the cell, thereby suppressing tumor cell proliferation in said subject,
   wherein the HE4 level in said tumor cell is >400 pM,
   wherein said level of HE4 in said tumor cell is inhibited by administering an effective amount of an HE4 inhibitor to said tumor cell,
   wherein the ICI comprises PD-L1,
   wherein the level of said one or more ICIs in said tumor cell is inhibited by administering an effective amount of an ICI inhibitor to said tumor cell, and
   wherein said tumor cell is a Müllerian cancer cell.

2. The method of claim 1, wherein said tumor cell comprises a malignant tumor cell.

3. The method of claim 2, wherein said malignant tumor cell is an ovarian cancer cell, an endometrial cancer cell, or a breast cancer cell.

4. The method of claim 1, wherein said HE4 inhibitor comprises a neutralizing anti-HE4 antibody, an antisense oligonucleotide, a small interfering ribonucleic acid (siRNA), a small hairpin RNA (shRNA), a non-antibody binding polypeptide, or a small molecule chemical compound.

5. The method of claim 1, wherein said level of HE4 in said tumor cell is inhibited with

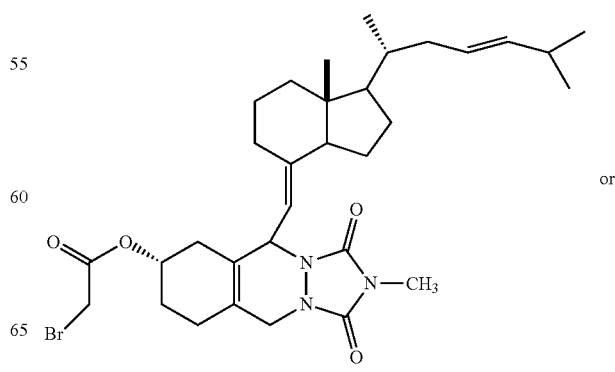

-continued

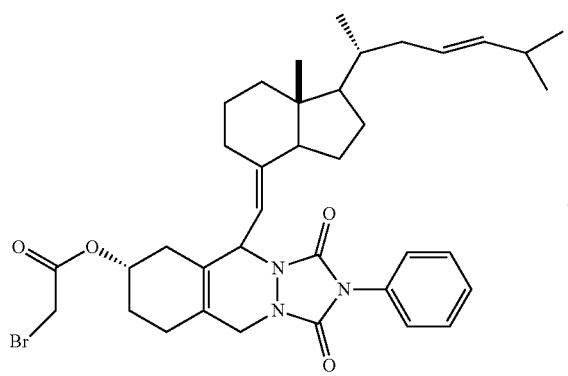

PT19c

6. The method of claim 4, wherein said HE4 inhibitor comprises an antisense oligonucleotide.

7. The method of claim 6, wherein the antisense oligonucleotide comprises a Locked Nucleic Acid (LNA) longRNA GAPmer comprising a sequence of 5'-TTGCTGAAAGTGGTTA-3' (SEQ ID NO:1) or 5'-AGAGTCCCGAAAAAGG-3'(SEQ ID NO:2).

8. The method of claim 1 wherein said one more ICIs are selected from the group consisting of CD80, CD28, CD86, cytotoxic T-lymphocyte-associated protein 4 (CTLA-4), programmed death-ligand 1 (PD-L1), programmed death-ligand 2 (PD-L2), programmed cell death protein 1 (PD-1), Ligand of Inducible T-cell costimulator (L-ICOS), Inducible T-cell costimulator (ICOS), CD276, and V-set domain containing T cell activation inhibitor 1 (VTCN1).

9. The method of claim 1, wherein the ICI inhibitor is selected from the group consisting of a neutralizing anti-ICI antibody, an antisense oligonucleotide, a small interfering ribonucleic acid (siRNA), a small hairpin RNA (shRNA), a non-antibody binding polypeptide, or a small molecule chemical compound.

10. The method of claim 9, wherein the ICI inhibitor comprises a small molecule chemical compound.

11. The method of claim 10, wherein the small molecule chemical compound is selected from the group consisting of:

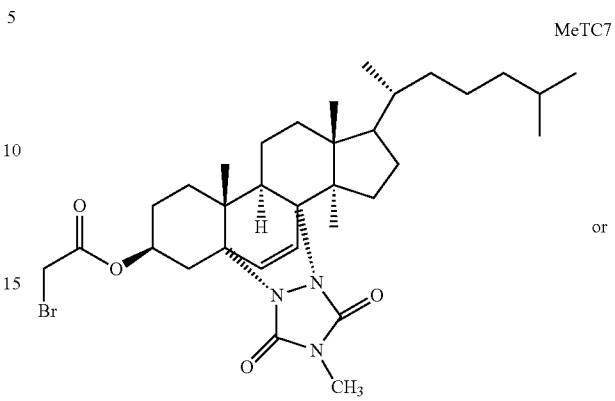

MeTC7 or

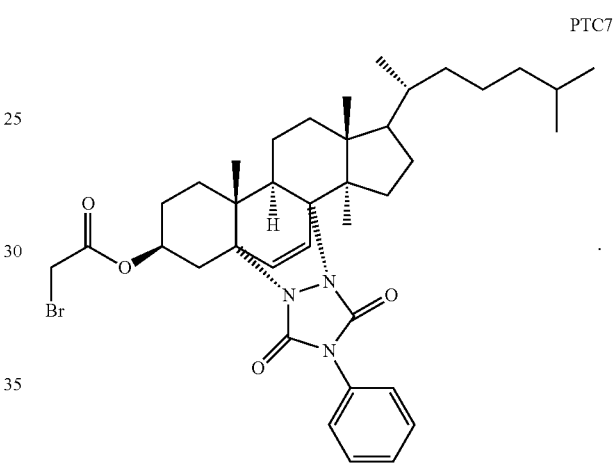

PTC7

* * * * *

UNITED STATES PATENT AND TRADEMARK OFFICE
CERTIFICATE OF CORRECTION

PATENT NO. : 10,376,535 B2  
APPLICATION NO. : 15/561466  
DATED : August 13, 2019  
INVENTOR(S) : Richard G. Moore, Rakesh K. Singh and Naohiro Yano Page 1 of 2

It is certified that error appears in the above-identified patent and that said Letters Patent is hereby corrected as shown below:

In the Claims

At Column 50, Line 5, the structure reading:

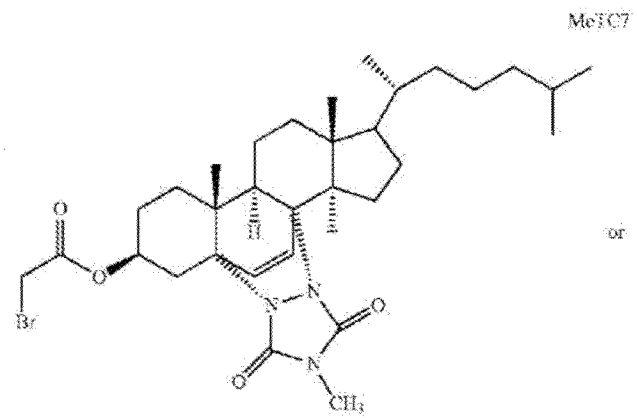

Should read:

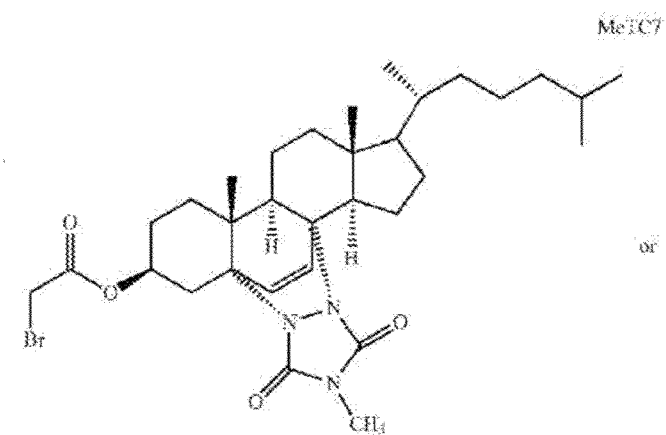

Signed and Sealed this  
Thirty-first Day of December, 2019

Andrei Iancu  
*Director of the United States Patent and Trademark Office*

CERTIFICATE OF CORRECTION (continued)
U.S. Pat. No. 10,376,535 B2

At Column 50, Line 22, the structure reading:

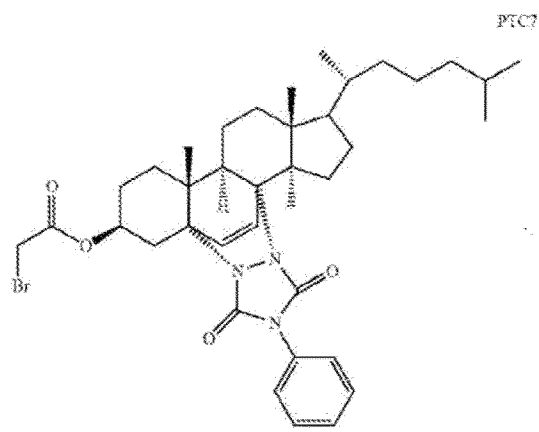

,

Should read:

SEQUENCE LISTING

```
<160> NUMBER OF SEQ ID NOS: 7

<210> SEQ ID NO 1
<211> LENGTH: 16
<212> TYPE: DNA
<213> ORGANISM: Artificial Sequence
<220> FEATURE:
<223> OTHER INFORMATION: Synthetic primer

<400> SEQUENCE: 1
ttgctgaaag tggtta                                                    16

<210> SEQ ID NO 2
<211> LENGTH: 15
<212> TYPE: DNA
<213> ORGANISM: Artificial Sequence
<220> FEATURE:
<223> OTHER INFORMATION: Synthetic Primer

<400> SEQUENCE: 2
gagtcccgaa aaagg                                                     15

<210> SEQ ID NO 3
<211> LENGTH: 15
<212> TYPE: DNA
<213> ORGANISM: Artificial Sequence
<220> FEATURE:
<223> OTHER INFORMATION: Synthetic Primer

<400> SEQUENCE: 3
```

```
aacacgtcta tacgc                                               15

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
gcctgtgttc tctgtggact                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
acaatggtgg catactccgt                                          20

<210> SEQ ID NO 6
<211> LENGTH: 19
<212> TYPE: DNA
<213> ORGANISM: Artificial Sequence
<220> FEATURE:
<223> OTHER INFORMATION: Synthetic Primer

<400> SEQUENCE: 6
aatcccatca ccatcttcc                                           19

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
gtccttccac gataccaaag                                          20
```